(12) United States Patent
Sakai

(10) Patent No.: US 10,631,852 B2
(45) Date of Patent: *Apr. 28, 2020

(54) MEDICAL SUTURING INSTRUMENT

(71) Applicant: Covidien AG, Neuhausen am Rheinfall (CH)

(72) Inventor: Yosuke Sakai, Shizuoka (JP)

(73) Assignee: Covidien AG, Neuhausen am (CH)

( * ) Notice: Subject to any disclaimer, the term of this patent is extended or adjusted under 35 U.S.C. 154(b) by 246 days.

This patent is subject to a terminal disclaimer.

(21) Appl. No.: 15/851,573

(22) Filed: Dec. 21, 2017

(65) Prior Publication Data

US 2018/0185021 A1 Jul. 5, 2018

Related U.S. Application Data

(63) Continuation of application No. 14/406,455, filed as application No. PCT/US2013/045624 on Jun. 13, 2013, now Pat. No. 9,877,715.

(30) Foreign Application Priority Data

Jun. 18, 2012 (JP) .................................. 2012-137184

(51) Int. Cl.
*A61B 17/04* (2006.01)
*A61B 17/12* (2006.01)
(Continued)

(52) U.S. Cl.
CPC ...... *A61B 17/0469* (2013.01); *A61B 17/0485* (2013.01); *A61B 2017/0053* (2013.01);
(Continued)

(58) Field of Classification Search
CPC ............ A61B 17/0469; A61B 17/0485; A61B 2017/0053; A61B 2017/00526;
(Continued)

(56) References Cited

U.S. PATENT DOCUMENTS

| 5,364,410 A | 11/1994 | Failla et al. |
| 5,431,666 A | 7/1995 | Sauer et al. |

(Continued)

FOREIGN PATENT DOCUMENTS

| JP | 2009-213763 A | 9/2009 |
| JP | 2010-240418 A | 10/2010 |
| WO | 2007/129431 A1 | 11/2007 |

OTHER PUBLICATIONS

Japanese Notification of Reasons for Refusal issued in corresponding application No. 2012-137184 dated Dec. 22, 2015.
(Continued)

*Primary Examiner* — Amy R Weisberg
(74) *Attorney, Agent, or Firm* — Carter, DeLuca & Farrell LLP

(57) ABSTRACT

A medical suturing instrument in which the movement of an operation part is transmitted with a time lag to a loop forming part and a suture thread by means of a loop feed/return mechanism and a suture thread feed mechanism, and once a loop has been fed out from the tip end of a loop introduction needle, the suture thread is fed out from the tip end of a suture thread introduction needle.

20 Claims, 8 Drawing Sheets

(51) Int. Cl.
*A61B 17/00* (2006.01)
*A61B 17/06* (2006.01)

(52) U.S. Cl.
CPC .............. *A61B 2017/00526* (2013.01); *A61B 2017/00818* (2013.01); *A61B 2017/0472* (2013.01); *A61B 2017/061* (2013.01); *A61B 2017/06052* (2013.01); *Y10T 29/49826* (2015.01)

(58) Field of Classification Search
CPC .... A61B 2017/061; A61B 2017/06052; A61B 2017/0472; A61B 2017/00818; Y10T 29/49826
See application file for complete search history.

(56) References Cited

U.S. PATENT DOCUMENTS

| | | |
|---|---|---|
| 5,462,560 A | 10/1995 | Stevens |
| 5,474,568 A | 12/1995 | Scott |
| 5,478,344 A | 12/1995 | Stone et al. |
| 5,527,321 A | 6/1996 | Hinchliffe |
| 5,540,704 A | 7/1996 | Gordon et al. |
| 5,586,986 A | 12/1996 | Hinchliffe |
| 5,613,974 A | 3/1997 | Andreas et al. |
| 5,700,272 A | 12/1997 | Gordon et al. |
| 5,700,273 A | 12/1997 | Buelna et al. |
| 5,722,981 A | 3/1998 | Stevens |
| 5,741,278 A | 4/1998 | Stevens |
| 5,779,719 A | 7/1998 | Klein et al. |
| 5,836,956 A | 11/1998 | Buelna et al. |
| 5,846,253 A | 12/1998 | Buelna et al. |
| 5,860,990 A | 1/1999 | Nobles et al. |
| 5,948,001 A | 9/1999 | Larsen |
| 6,059,800 A | 5/2000 | Hart et al. |
| 6,203,554 B1 | 3/2001 | Roberts |
| 6,296,648 B1 | 10/2001 | Bootle et al. |
| 6,355,050 B1 | 3/2002 | Andreas et al. |
| 6,517,553 B2 | 2/2003 | Klein et al. |
| 6,551,329 B1 | 4/2003 | Kortenbach et al. |
| 6,551,330 B1 | 4/2003 | Bain et al. |
| 6,551,331 B2 | 4/2003 | Nobles et al. |
| 6,896,685 B1 | 5/2005 | Davenport |
| 6,939,357 B2 | 9/2005 | Navarro et al. |
| 7,918,868 B2 | 4/2011 | Marshall et al. |
| 8,109,943 B2 | 2/2012 | Boraiah et al. |
| 8,317,679 B2 | 11/2012 | Surti |
| 8,672,955 B2 | 3/2014 | Nagata et al. |
| 9,693,767 B1 | 7/2017 | Foreman |
| 2005/0043746 A1 | 2/2005 | Pollak et al. |
| 2007/0179509 A1 | 8/2007 | Nagata et al. |
| 2007/0282351 A1 | 12/2007 | Harada et al. |
| 2008/0200931 A1 | 8/2008 | Harada et al. |
| 2009/0318939 A1 | 12/2009 | Funamura et al. |
| 2010/0228271 A1* | 9/2010 | Marshall ............ A61B 17/0469 606/144 |
| 2011/0082477 A1 | 4/2011 | Smith |
| 2011/0288563 A1 | 11/2011 | Gianotti et al. |
| 2011/0295279 A1 | 12/2011 | Stone et al. |
| 2012/0010634 A1 | 1/2012 | Crabb et al. |
| 2013/0012962 A1 | 1/2013 | Stone |
| 2015/0142019 A1 | 5/2015 | Sakai |

OTHER PUBLICATIONS

Japanese Notification of Reasons for Refusal issued in corresponding application No. 2012-137184 dated Dec. 22, 015.

* cited by examiner

MEDICAL SUTURING INSTRUMENT

CROSS-REFERENCE TO RELATED APPLICATIONS

This application is a continuation of U.S. patent application Ser. No. 14/406,455 filed Dec. 8, 2014, which is a National Stage Application of PCT/US13/45624 filed Jun. 13, 2013, which claims benefit of and priority to Japan Patent Application No. 2012-137184 filed Jun. 18, 2012, and the disclosures of each of the above-identified applications are hereby incorporated by reference in their entirety.

BACKGROUND

Technical Field

The present invention relates to a medical suturing instrument which is used when suture thread for holding the wall of an internal organ such as the stomach or bladder from outside the body on the body surface-side, such as the abdominal wall, is introduced into the internal organ, and when the suture thread is withdrawn from inside the internal organ.

Related Art

People with a reduced function for ingesting food orally under their own power due to advanced age or illness (referred to below as "patients") are administered with enteral feeding in which liquid food and nutrients etc. are supplied using a gastrostomy catheter. When percutaneous endoscopic gastrostomy (PEG) is used, for example, a through-hole (e.g., a fistula such as a gastric fistula) which runs through the patient's abdominal wall and the wall of an internal organ (stomach wall) is established, the gastrostomy catheter is fitted into the through-hole, and the patient is supplied with liquid food etc. through the gastrostomy catheter.

When the through-hole is established, the wall of an internal organ which readily moves and the abdominal wall are normally sutured and fixed percutaneously using suture thread in order to simplify formation of the through-hole. Various kinds of medical suturing instruments have been proposed for use in suturing and fixing the internal organ wall and the abdominal wall.

An instrument of this kind which is disclosed is a medical instrument "which houses, inside a case main body, a feed-out mechanism for successively feeding out towards the tip end a suture thread inserted into a suture thread insertion puncture needle 20 from the base end thereof; and a projection mechanism for causing an annular member of a stylet housed inside a suture thread gripping puncture needle 30 to project from the tip end of the suture thread gripping puncture needle 30," for example, as described with reference to FIGS. 5 and 6 in Japanese Patent Application Nos. JP2009-213763A and JP2009-213764A. This medical instrument is designed to make it possible for only one practitioner or for a practitioner and an assistant to efficiently and safely form a ligature inside the body.

SUMMARY

With medical instruments such as those disclosed in in the above-referenced Japanese patent applications, the practitioner has to insert the suture thread into the medical instrument, which increases the practitioner's workload. Furthermore, the operation involving insertion of the suture thread is often complex, so it is not a simple matter to perform. The following operations are further needed with medical instruments such as those disclosed in the above-referenced Japanese patent applications, namely: an operation in which punctures are made in the stomach from the abdominal wall using the suture thread insertion puncture needle and the suture thread gripping puncture needle, after which a stylet is pushed in in order to form the annular shape of the annular member; an operation in which an operating roller is turned in order to insert the suture thread into the stomach; and an operation in which a release button is pressed in order to grip the suture thread with the annular member, all of which make the operating procedure more extensive.

One or more aspects of the present invention can be directed to a medical suturing instrument which is far easier to use and to handle than those described, for example, in Japanese Patent Application Nos. JP2009-213763A and JP2009-213764A.

The medical suturing instrument according to one or more aspects of the present invention enables the suture thread to be introduced into an internal organ and to be withdrawn therefrom simply by pushing and pulling the operation part, and therefore the work of the practitioner can be considerably reduced and the ease of use is very much improved.

According to one or more aspects a medical suturing instrument includes a housing, a loop introduction needle at a tip end of the housing, a suture thread introduction needle having a portion of a suture thread disposed therein, the suture thread introduction needle disposed at the tip end of the housing at a prescribed distance apart from the loop introduction needle and oriented substantially parallel thereto, a loop forming part having a loop in a tip end thereof, the loop insertable into the loop introduction needle, a loop feed/return mechanism inside the housing and operatively disposed to move the loop forming part, a suture thread feed mechanism inside the housing and operatively disposed to feed the suture thread; and an operation part operatively coupled to the loop feed/return mechanism and the suture thread feed mechanism.

In the medical suturing instrument according to one or more aspects, the operation part has a first position that moves the loop feed/return mechanism into feeding the loop out from the loop introduction needle, and moves the suture thread feed mechanism into feeding the thread out from the suture thread introduction needle. According to a further embodiment, the operation part has a second position that retracts the loop feed/return mechanism and the suture thread feed mechanism to return the loop at least partly inside the loop introduction needle after the suture thread has been gripped by the loop.

In the medical suturing instrument according to one or more aspects, a first abutment part is provided in the loop feed/return mechanism, and a second abutment part is provided in the suture thread feed mechanism. According to one embodiment a distance between the first abutment part and the second abutment part when the suture thread is gripped by the loop at a tip end of the loop introduction needle is selected such that a movement of the operation part to the second position is transmitted to the suture thread feed mechanism by way of the loop feed/return mechanism after the suture thread has been gripped at the tip end of the loop introduction needle or at the same time as the suture thread is gripped at the tip end of the loop introduction needle.

In the medical suturing instrument according to one or more aspects, the loop feed/return mechanism includes an elastic member to which movement of the operation part is transmitted, and a loop feed/return part which moves by way of the elastic member to feed/return the loop forming part, the suture thread feed mechanism includes a first hollow member which is at least fixed to the base end side of the housing and has the suture thread inserted therein, a suture thread feed part to which the movement of the operation part is transmitted, a second hollow member including a hollow part through which the first hollow member can pass, to which the movement of the operation part is transmitted by way of the suture thread feed part, and a suture thread clamping member fitted to the suture thread feed part in order to clamp the first hollow member, suture thread or second hollow member according to the position of the suture thread feed part.

According to one embodiment, in the loop feed/return mechanism, after the loop feed/return part has stopped moving, movement of the operation part is transmitted only to the elastic member so that the elastic member is compressed and the shape of the loop is maintained as a result. According to a further embodiment, in the suture thread feed mechanism, after the loop feed/return part has stopped moving, the movement of the operation part is transmitted, and the suture thread clamping member which starts to move together with the suture thread feed part withdraws from the first hollow member while pushing the second hollow member to clamp the suture thread, and the suture thread is fed out from a tip end of the suture thread introduction needle in such a way as to be inserted into the loop which is already being fed out or is starting to be fed out.

In the medical suturing instrument according to one or more aspects, the first abutment part is provided in the loop feed/return part, the second abutment part is provided in the suture thread feed part in such a way as to be able to abut the first abutment part and the operation part. According to one embodiment, when the loop feed/return part is no longer moving and the movement of the operation part is transmitted to the elastic member, the operation part and the second abutment part come into abutment, and the movement of the operation part is transmitted to the suture thread feed mechanism side.

In the medical suturing instrument according to one or more aspects, the suture thread feed mechanism includes a first projection extending radially therefrom, the loop feed return mechanism includes a second projection configured to travel forward when the operation part is moved to the first position. According to a further embodiment, contact between the first projection and the second projection as the operation part moves to the second position transmits rearward force to the suture thread feed mechanism, and a distance separating the first projection from the second projection when the operation part is in the first position is selected such that the contact between the first projection and the second projection as the operation part moves to the second position occurs at or following the suture thread being gripped at the tip end of the loop introduction needle.

According to one or more further aspects a medical suturing instrument includes a housing, a loop introduction needle which is provided at a tip end of the housing, a suture thread introduction needle for housing a suture thread, the suture thread introduction needle provided at the tip end of the housing a prescribed distance apart from the loop introduction needle and substantially parallel thereto, a loop forming part which has a loop formed at a tip end thereof and is movably inserted into the loop introduction needle, a loop feed/return mechanism provided inside the housing for moving the loop forming part, a suture thread feed mechanism provided inside the housing for feeding out the suture thread, and an operation part which is provided inside the housing or projecting from the housing, and which moves the loop feed/return mechanism and the suture thread feed mechanism.

In the medical suturing instrument according to one or more aspects, movement of the operation part is transmitted to the loop feed/return mechanism, and the loop is fed out from a tip end of the loop introduction needle, movement of the operation part is transmitted to the suture thread feed mechanism, and the suture thread is fed out from a tip end of the suture thread introduction needle.

In the medical suturing instrument according to one or more aspects, following the loop being fed out from the tip end of the loop introduction needle and the suture thread fed out from the tip end of the suture thread introduction needle, movement of the operation part in the opposite direction is transmitted to the loop feed/return mechanism, and the loop is housed inside the loop introduction needle, and further the movement of the operation part in the opposite direction is transmitted to the suture thread feed mechanism after the suture thread has been gripped by the loop at the tip end of the loop introduction needle or at the same time as the suture thread is gripped by the loop at the tip end of the loop introduction needle.

In the medical suturing instrument according to one or more aspects, a first abutment part is provided in the loop feed/return mechanism, a second abutment part which can abut the first abutment part is provided in the suture thread feed mechanism, and a distance between the first abutment part and the second abutment part when the suture thread is gripped by the loop at the tip end of the loop introduction needle is adjusted in such a way that the movement of the operation part in the opposite direction is transmitted to the suture thread feed mechanism by way of the loop feed/return mechanism after the suture thread has been gripped at the tip end of the loop introduction needle or at the same time as the suture thread is gripped at the tip end of the loop introduction needle.

In the medical suturing instrument according to one or more aspects, the loop feed/return mechanism comprises an elastic member to which movement of the operation part is transmitted, and a loop feed/return part which moves by way of the elastic member to feed/return the loop forming part, the suture thread feed mechanism comprises a first hollow member which is at least fixed to the base end side of the housing and has the suture thread inserted therein, a suture thread feed part to which the movement of the operation part is transmitted, a second hollow member comprising a hollow part through which the first hollow member can pass, to which the movement of the operation part is transmitted by way of the suture thread feed part, and a suture thread clamping member fitted to the suture thread feed part in order to clamp the first hollow member, suture thread or second hollow member according to the position of the suture thread feed part.

In the medical suturing instrument according to one or more aspects, in the loop feed/return mechanism, after the loop feed/return part has stopped moving, movement of the operation part is transmitted only to the elastic member so that the elastic member is compressed and the shape of the loop is maintained as a result, and the suture thread feed mechanism, after the loop feed/return part has stopped moving, the movement of the operation part is transmitted, and the suture thread clamping member which starts to move together with the suture thread feed part withdraws from the first hollow member while pushing the second hollow member to clamp the suture thread, and the suture thread is fed out from the tip end of the suture thread introduction needle in such a way as to be inserted into the loop which is already being fed out or is starting to be fed out.

In the medical suturing instrument according to one or more aspects, the first abutment part is provided in the loop feed/return part, the second abutment part is provided in the suture thread feed part in such a way as to be able to abut the first abutment part and the operation part, and, when the loop feed/return part is no longer moving and the movement of the operation part is transmitted to the elastic member, the operation part and the second abutment part come into abutment, and the movement of the operation part is transmitted to the suture thread feed mechanism side.

According to one or more still further aspects, a suturing method employing a medical suturing instrument is provided where the medical suturing instrument includes a housing, a loop introduction needle at a tip end of the housing, a suture thread introduction needle disposed at the tip end of the housing and configured to accommodate a suture thread therewithin, a loop forming part having a loop in a tip end thereof, the loop insertable into the loop introduction needle, a loop feed/return mechanism inside the housing, a suture thread feed mechanism inside the housing and an operation part coupled to the loop feed/return mechanism and the suture thread feed mechanism. According to some embodiments, the method includes acts of: inserting the loop introduction needle and the suture thread introduction needle into an internal organ located within a body, moving the operating part to a first position to feed the loop out a distal end of the loop introduction needle and to feed the suture thread out a distal end of the suture thread introduction needle, moving the operating part to a second position to retract the loop feed/return mechanism and the suture thread feed mechanism and return the loop at least partly inside the loop introduction needle after the suture thread has been gripped by the loop, withdrawing the loop introduction needle and the suture thread introduction needle outside the body, and releasing the suture thread from the loop for fastening to another portion of the suture thread extending from the body.

In the method according to one or more aspects, the suture thread feed mechanism includes a first projection extending radially therefrom, the loop feed return mechanism includes a second projection configured to travel forward when the operation part is moved to the first position. According to one embodiment, the method further includes transmitting a rearward force to the suture thread feed mechanism via contact between the first projection and the second projection as the operation part moves to the second position; and selecting a distance separating the first projection from the second projection when the operation part is in the first position such that the contact between the first projection and the second projection as the operation part moves to the second position occurs at or following the suture thread being gripped at the tip end of the loop introduction needle.

In the method according to one or more aspects, the loop feed/return mechanism includes an elastic member, and a loop feed/return part, and the suture thread feed mechanism comprises a first hollow member which is at least fixed to the base end side of the housing and has the suture thread inserted therein, a suture thread feed part, a second hollow member includes a hollow part through which the first hollow member can pass, and a suture thread clamping member fitted to the suture thread feed part in order to clamp the first hollow member, suture thread or second hollow member according to the position of the suture thread feed part.

According to one embodiment, the method further includes acts of: moving the loop feed/return part by way of the elastic member for feeding and return of the loop forming part, transmitting movement of the operation part to the suture thread feed part, transmitting movement of the operation part to the second hollow member by way of the suture thread feed part, in the loop feed return mechanism, maintaining the shape of the loop, after the loop feed/return part has stopped moving, by only transmitting movement of the operation part to the elastic member to compress the elastic member, in the suture thread feed mechanism, after the loop feed/return part has stopped moving, transmitting movement of the operation part to move the suture thread clamping member together with the suture thread feed part being withdrawn from the first hollow member while pushing the second hollow member to clamp the suture thread, and feeding the suture thread out from the tip end of the suture thread introduction needle in such a way as to be inserted into the loop which is already being fed out or is starting to be fed out.

In the method according to one or more aspects the method includes acts of, including the first projection in the suture thread feed part to allow the first projection to contact both the second projection and the operation part, including the second projection in the loop feed return part, transmitting movement of the operation part to the elastic member with the loop feed return part stationary, and transmitting the movement of the operation part to the suture thread feed mechanism with the first projection in contact with the operation part with the loop feed return part stationary.

One or more aspects of the invention can be directed to a method of fabricating a medical suturing instrument having a housing. The method can comprise providing a loop introduction needle at a tip end of a housing; disposing a suture thread introduction needle having a portion of a suture thread disposed therein at the tip end of the housing at a prescribed distance apart from the loop introduction needle and oriented substantially parallel thereto; providing a loop forming part having a loop in a tip end thereof such that the loop is insertable into the loop introduction needle; disposing a loop feed/return mechanism inside the housing such that the loop feed/return mechanism is operatively disposed to move the loop forming part; disposing a suture thread feed mechanism inside the housing such that the suture thread feed mechanism is operatively disposed to feed the suture thread; and operatively coupling an operation part to the loop feed/return mechanism and the suture thread feed mechanism, wherein the operation part has a first position that moves the loop feed/return mechanism into feeding the loop out from the loop introduction needle, and moves the suture thread feed mechanism into feeding the thread out from the suture thread introduction needle, and wherein the operation part has a second position that retracts the loop feed/return mechanism and the suture thread feed mechanism to return the loop at least partly inside the loop introduction needle after the suture thread has been gripped by the loop.

DETAILED DESCRIPTION

Figure 1:
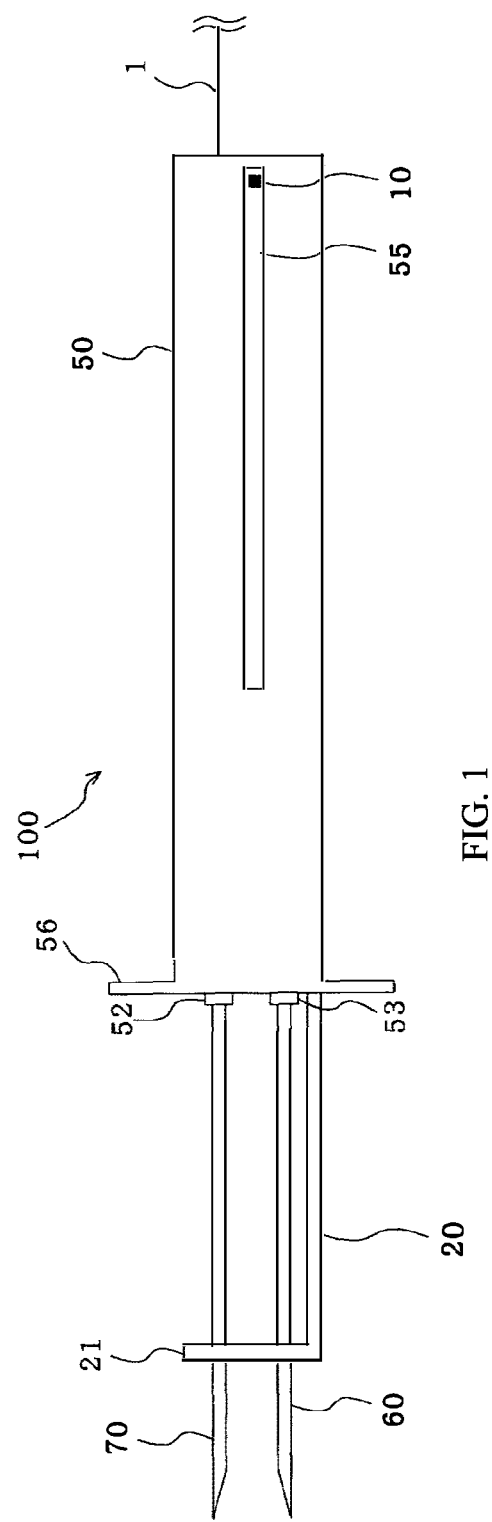
FIG. 1 is a schematic external view showing an example of the structure of the medical suturing instrument according to one or more embodiments of the invention.
Figure 2:
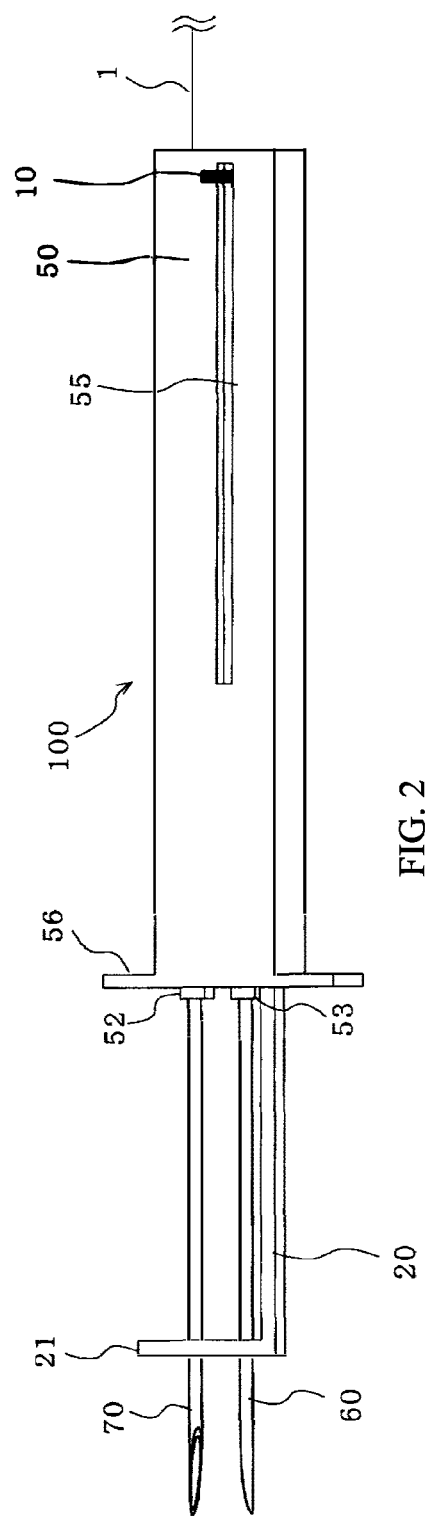
FIG. 2 is a schematic oblique view showing the external structure of the medical suturing instrument according to one or more embodiments of the invention.
Figure 3:
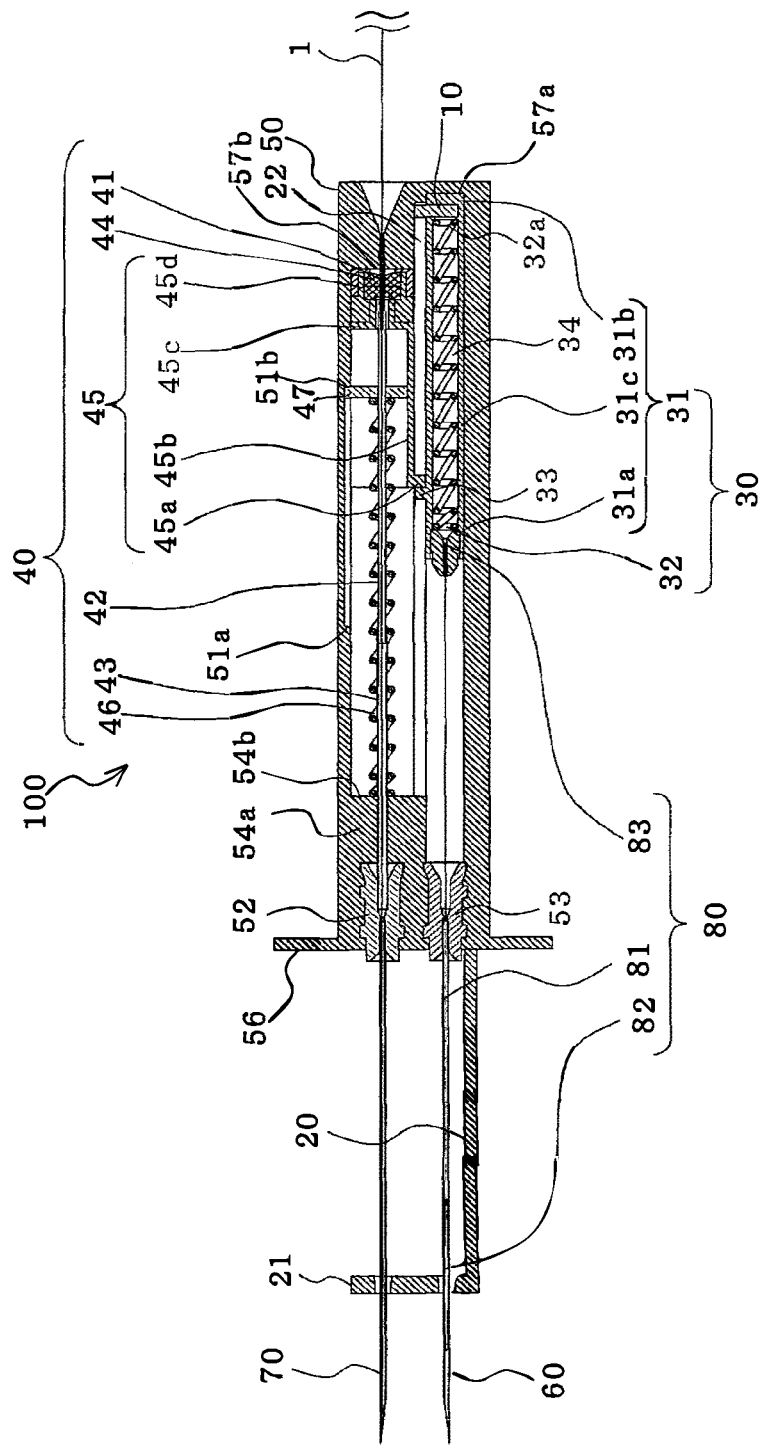
FIG. 3 is a schematic internal structural diagram showing an example of the internal structure of the medical suturing instrument according to one or more embodiments of the invention.

Non-limiting embodiments of the present invention will be exemplarily described below with reference to the accompanying drawings FIG. 1 is a schematic external view showing one example of the structure of the medical suturing instrument according to an embodiment of the present invention (referred to below simply as the "suturing instrument 100"). FIG. 2 is a schematic oblique view showing the external structure of the suturing instrument 100. FIG. 3 is a schematic internal structural diagram showing one example of the internal structure of the suturing instrument 100. The structure and operation of the suturing instrument 100 will be described with reference to FIGS. 1 to 3. The suturing instrument 100 is used in order to facilitate formation of a fistula for insertion of a fistula catheter when suture thread for lifting the wall of an internal organ such as the stomach or bladder from outside the body towards the abdominal wall and holding it in place is introduced into the internal organ. It should be noted that the size relationships of the structural components in the figures below may differ from the actual size relationships, including in FIG. 1.

The suturing instrument 100 externally comprises: a housing 50; an operation part 10 which is operated by the practitioner; a loop introduction needle 60 which is provided at the tip end of the housing 50; and a suture thread introduction needle 70 which is provided at the tip end of the housing 50 a prescribed distance apart from the loop introduction needle 60 and substantially parallel thereto. The suturing instrument 100 also comprises, inside the housing 50, a loop feed/return mechanism 30 which operates in conjunction with the movement of the operation part 10; and a suture thread feed mechanism 40 which operates in conjunction with the movement of the operation part 10. The suturing instrument 100 further comprises a loop forming part 80 which is movably inserted inside the loop introduction needle 60.

It should be noted that FIGS. 1 to 3 also show a suture thread 1 which is fed out from the tip end (blade edge) of the suture thread introduction needle 70 by means of the suture thread feed mechanism 40. Furthermore, the tip end side denotes the side which is inserted into the patient (patient side), while the base end side denotes the side which is operated by the practitioner (operation side). In the description which follows, the tip end side may also be referred to as forwards or the front, and the base end side may also be referred to as backwards or the rear. The suture thread 1 has a length sufficient for multiple procedures.

The suture thread 1 does not form part of the suturing instrument 100, but it will be described briefly as it serves as an organopexy tool. The suture thread 1 should be made of a material which is sufficiently flexible that it can bend along bodily tissues when inserted inside the body, and which also has sufficient tensile strength that it can lift internal organs (nylon yarn, for example). Furthermore, the suture thread 1 is cut when fitted to or removed from the patient. For this reason, the suture thread 1 is preferably made of a material and has a diameter size that can be cut by an instrument found in a medical setting, such as scissors. Furthermore, the suturing instrument 100 is made to pierce the patient with the suture thread 1 inserted up to the tip end of the suture thread introduction needle 70.

The housing 50 has a hollow, substantially cuboid shape which is rectangular in the front-to-rear direction. The housing 50 accommodates the loop feed/return mechanism 30 and the suture thread feed mechanism 40. The loop feed/return mechanism 30 and the suture thread feed mechanism 40 are accommodated substantially in parallel inside the housing 50, and they can move backwards and forwards inside the housing 50. The housing 50 forms the unit of the suturing instrument 100 as a whole and constitutes the part which is actually held by the practitioner during a procedure. It should be noted that the housing 50 does not have to be substantially cuboid in shape, and there is no particular limitation as to the external shape thereof. Furthermore, the housing 50 may simply consist of a skeleton. That is, the housing 50 should have a structure which enables the other components (to be described later) to function.

Furthermore, the loop introduction needle 60 and the suture thread introduction needle 70 are fitted a prescribed distance apart and substantially parallel to each other at the tip end of the housing 50. For example, as shown in FIG. 3, support parts (support part 52, support part 53) may be provided at the tip end of the housing 50, and the loop introduction needle 60 and the suture thread introduction needle 70 may be inserted into the support parts so that the loop introduction needle 60 and the suture thread introduction needle 70 are detachably supported. The support parts should, for example, comprise a material such as synthetic resin which is moulded into a substantially cuboid shape, a substantially cylindrical shape, or a plurality of these shapes combined (a plurality of substantially cuboid shapes combined, a plurality of substantially cylindrical shapes combined, or a combination of substantially cuboid shapes and substantially cylindrical shapes). Furthermore, multiple protrusions may be provided on the outer periphery of the support parts, as shown in the figures. It should be noted that the support parts may equally be designed in such a way as not to project from the tip end side of the housing 50.

Moreover, the base ends of the loop introduction needle 60 and the suture thread introduction needle 70 may already be supported by support members which are detachably fitted to the tip end of the housing 50. Furthermore, the loop introduction needle 60 and the suture thread introduction needle 70 may already be fixed to the housing 50. In addition, the loop introduction needle 60 and the suture thread introduction needle 70 do not have to be fitted to the very tip end of the housing 50, provided that they are fitted towards the tip end of the housing 50. That is, the base ends of the loop introduction needle 60 and the suture thread introduction needle 70 should extend into the housing 50.

The tip end side of the suture thread feed mechanism 40 in the housing 50 has a predetermined thickness such that a third hollow member 43 which forms part of the suture thread feed mechanism 40 is supported as it passes therethrough. The section having a predetermined thickness on the tip end side of the suture thread feed mechanism 40 in the housing 50 is referred to as the "thick-walled part 54a". Furthermore, the inner wall surface on the tip end side of the suture thread feed mechanism 40 in the housing 50, that is, the surface of the thick-walled part 54a on the suture thread feed mechanism 40 side, is simply referred to as the "inner wall surface 54b". In other words, in the construction of the housing 50 shown in FIG. 3, the inner wall surface 54b is formed only on the suture thread feed mechanism 40 side. However, the construction of the housing 50 is not limited to what is shown in FIG. 3, and the thick-walled part 54a may be provided on the loop feed/return mechanism 30 side.

The tip end of a second elastic member 46 which forms part of the suture thread feed mechanism 40 abuts the inner wall surface 54b. Furthermore, a first abutment part 33 which forms part of a loop feed/return part 31 (to be described later) also abuts the inner wall surface 54b. When the first abutment part 33 which forms part of the loop feed/return part 31 abuts the inner wall surface 54b, the loop feed/return part 31 does not move any further forwards.

A through-hole for supporting a first hollow member 41 which forms part of the suture thread feed mechanism 40 is formed in the base end-side wall of the housing 50 on the suture thread feed mechanism 40 side. FIG. 3 shows an example in which the base end side of the through-hole is formed as a taper which grows smaller in diameter towards the tip end side. Furthermore, FIG. 3 shows an example in which the first hollow member 41 is fitted in and supported by the through-hole, excluding the tapered portion thereof. However, the structure for supporting the first hollow member 41 is not limited to the structure shown in FIG. 3, and the first hollow member 41 may be supported without forming a tapered portion in the through-hole, or the base end of the first hollow member 41 may be supported in such a way as to project outwards of the housing 50. Furthermore, a support member similar to the support parts (support part 52, support part 53) may be attached to the base end side of the housing 50 on the suture thread feed mechanism 40 side in order to support the first hollow member 41. In this case, the first hollow member 41 may be attached to or detached from the housing 50 after attachment to the support member.

Furthermore, a stopper 51a and a stopper 51b are formed on part of the inner wall surface of the housing 50. The stopper 51a and the stopper 51b may be formed to cause part of the inner wall surface of the housing 50 to project into the housing 50, or may be formed by providing a step on part of the inner wall surface of the housing 50. The stopper 51a and the stopper 51b have the function of regulating the forwards and backwards movement of the movement regulating member 47 which is fixed to the second hollow member 42. However, the stopper 51a is not required if the forwards movement of the second hollow member 42 is regulated by the tip end of the second hollow member 42 abutting the support part 52 or inner wall surface 54b, or abutting part of the inner wall of a third hollow member 43, or by the movement regulating member 47 abutting the base end of the third hollow member 43. It should be noted that if the tip end of the second hollow member 42 is made to abut the inner wall surface 54b, the third hollow member 43 is not provided.

Likewise, the stopper 51b is not required if the backwards movement of the second hollow member 42 is regulated by the base end of the second hollow member 42 abutting the outer wall of a first hollow member 41, or the tip end of the second hollow member 42 abutting the base end (inner side) of the third hollow member 43. Furthermore, if the tip end of the second hollow member 42 comes into abutment with the base end (inner side) of the third hollow member 43, the tip end of the second hollow member 42 projects radially outwards and the base end of the third hollow member 43 projects radially inwards, so the backwards movement of the second hollow member 42 may be regulated by the engagement of the two. It should be noted that the stopper 51a corresponds to the first stopper according to the present invention, and the stopper 51b corresponds to the second stopper according to the present invention.

Furthermore, a guide hole 55 which allows the operation part 10 to move forwards and backwards is formed in the lengthwise direction of the housing 50 in the side surface thereof. The guide hole 55 runs through the side surface of the housing 50 and is formed with a prescribed length. Moreover, there is no particular limitation as to the material from which the housing 50 is made, and a polyolefin such as polypropylene or polyethylene, or a synthetic resin such as polyvinyl chloride or polycarbonate may be employed. Moreover, a flange part 56 which projects radially outwards in the form of a rim is provided on the outer wall at the tip end of the housing 50. The flange part 56 serves to assist in the puncture operation.

A support rod 20 allowing forwards and backwards movement of a flat plate part 21 which is penetrated by the loop introduction needle 60 and the suture thread introduction needle 70 is provided on the housing 50. The flat plate part 21 can restrict changes in the distance between the loop introduction needle 60 and the suture thread introduction needle 70 by moving towards the tip end when the loop introduction needle 60 and the suture thread introduction needle 70 are made to pierce the patient's body. By providing this kind of flat plate part 21, it is possible to prevent flexing of the loop introduction needle 60 and the suture thread introduction needle 70 as well as any large changes in the distance therebetween. Furthermore, through the support rod 20, the flat plate part 21 can move forwards and backwards with respect to the loop introduction needle 60 and the suture thread introduction needle 70, so the flat plate part 21 does not present an obstruction to the piercing operation.

There is no particular limitation as to the planar shape of the flat plate part 21, but it may be rectangular, circular or polygonal. Furthermore, the tip end surface of the flat plate part 21 (the surface on the patient side) should be flat so as not to irritate the patient's skin. When this kind of flat plate part 21 is provided, the tip end of the support rod 20 extending parallel to the loop introduction needle 60 and the suture thread introduction needle 70 should be fixed to the flat plate part 21. Providing the support rod 20 makes it possible to reduce the force transmitted from the flat plate part 21 to the loop introduction needle 60 and the suture thread introduction needle 70, while also improving the stability of movement of the flat plate part 21.

The operation part 10 is operated by the practitioner when an organopexy tool is introduced into an internal organ using the suturing instrument 100. Furthermore, the operation part 10 serves to transmit the force applied by the practitioner to the loop feed/return mechanism 30 and the suture thread feed mechanism 40. The operation part 10 is disposed between the base end part 32*a* of a first elastic member 32 which forms part of the loop feed/return mechanism 30, and the base end part 31*b* of the loop feed/return part 31. The operation part 10 is provided partly inside the housing 50 or partly in the guide hole 55 of the housing 50 projecting from part of the side surface of the housing 50. Furthermore, the operation part 10 is able to move forwards and backwards along the guide hole 55. It should be noted that FIGS. 1 to 3 show an exemplary situation in which part of the operation part 10 is formed projecting from the guide hole 55.

Moreover, there is no particular limitation as to the material from which the operation part 10 is made, and it may be made from the same synthetic resin as the housing 50, or from a different material to that of the housing 50. Furthermore, there is no particular limitation as to the shape of the operation part 10, provided that it is a shape which can receive operations from the practitioner and allows practitioner operations to be transmitted to the loop feed/return mechanism 30 and the suture thread feed mechanism 40. Furthermore, a guide for moving the operation part 10 forwards and backwards in a straight line may be formed inside the housing 50 (the groove 22 shown in FIG. 3, for example).

FIGS. 1 to 3 show an example of the operation part 10 having a shape which projects outwards from the side surface of the housing 50 in a direction orthogonal to the direction of advance. By adopting such a shape, it is easy for the practitioner to catch the operation part 10 with the fingers, and the handling is improved. However, the shape of the operation part 10 is not restricted to the shape shown in FIGS. 1 to 3, and it is possible to extend the base end of the operation part 10 to the rear and to provide a rod which projects from the base end of the housing 50 so that the base end of the rod can be retractably inserted into the housing 50 to serve as the operation part 10. A button or the like may be provided at the base end of the rod in order to improve the handling. Furthermore, if the operation part 10 is provided inside the housing 50, a finger may be inserted through the guide hole 55 in order to operate the operation part 10.

The loop feed/return mechanism 30 operates in conjunction with the movement of the operation part 10 to cause the loop forming part 80, which is movably inserted into the loop introduction needle 60, to be fed out towards the tip end of the loop introduction needle 60 or to be returned inside the housing 50. The loop feed/return mechanism 30 comprises the loop feed/return part 31 and the first elastic member 32. It should be noted that the first elastic member 32 corresponds to the elastic member according to the present invention.

The loop feed/return part 31 comprises a tip end part 31*a*, the base end part 31*b*, a side wall part 31*c*, a first abutment part 33 and an accommodation part 34, and it can move forwards and backwards inside the housing 50 in response to the movement of the operation part 10. Moreover, the loop feed/return part 31 may, for example, comprise a hollow columnar member (cylindrical member) or a prismatic member (rectangular cylinder) or the like which can move forwards and backwards and in which the accommodation part 34 is formed such that the first elastic member 32 can be disposed therein. Furthermore, a cut (or incision) may be made in the side wall part 31*c* of the loop feed/return part 31 in order to allow communication between the accommodation part 34 and the outside. FIG. 3 shows an example of the loop feed/return part 31 with the suture thread feed mechanism 40 side open.

The tip end part 31*a* forms the tip end portion of the loop feed/return part 31, and a base end fixing part 83 of the loop forming part 80 is fixed thereto. The tip end part 31*a* is partially inserted into the support part 53 in a state in which the loop feed/return part 31 has been moved forwards. The base end part 31*b* forms the base end portion of the loop feed/return part 31 and the operation part 10 is disposed on the accommodation part 34 side thereof. The base end part 31*b* regulates the backwards movement of the loop feed/return part 31. That is, when the base end part 31*b* runs into the base end inner wall surface of the housing 50 (referred to below simply as the "inner wall surface 57*a*"), the loop feed/return part 31 cannot move any further backwards. It should be noted that the positions of the base end inner wall surfaces may differ on the loop feed/return mechanism 30 side and the suture thread feed mechanism 40 side, so the base end inner wall surface of the housing 50 on the suture thread feed mechanism 40 side will be referred to as the "inner wall surface 57*b*".

The side wall part 31*c* connects the tip end part 31*a* and the base end part 31*b*, and slidably abuts the inner wall surface inside the housing 50. However, the side wall part 31*c* does not have to cover the whole of the accommodation part 34, and a cut (or incision) may be formed therein in order to allow communication between the accommodation part 34 and the outside.

The first abutment part 33 has a base end surface in abutment with the tip end surface of a second abutment part 45*a* formed on a suture thread feed part 45 which forms part of the suture thread feed mechanism 40, and causes the suture thread feed part 45 to move backwards. Furthermore, as described above, the first abutment part 33 regulates the forwards movement of the loop feed/return part 31 by abutment with the inner wall surface 54*b*. The first abutment part 33 may be formed in the shape of a protrusion which projects from part of the side wall part 31*c* lying on the suture thread feed mechanism 40 side of the loop feed/return part 31, for example. Moreover, the shape of the first abutment part 33 is not limited to that of a protrusion, and it is sufficient for it to be able to transmit a backwards force to the suture thread feed part 45. Furthermore, the timing of abutment between the first abutment part 33 and the second abutment part 45*a* will be described in detail at a later stage.

The accommodation part 34 is a space enclosed by the tip end part 31*a*, base end part 31*b* and side wall part 31*c* of the loop feed/return part 31, and the first elastic member 32 is extendibly accommodated therein.

The first elastic member 32 consists of an elastic member which is extendible in the front-to-rear direction (for instance, a spring (coil spring, air spring etc.) or a rubber element). The first elastic member 32 is accommodated in the accommodation part 34 in a compressed state in which a force greater than the friction force of the loop 82 accommodated in the loop introduction needle 60 is applied thereto. That is, when the first elastic member 32 is accommodated in the accommodation part 34, it does not deform unless a force greater than the friction force of the loop 82 is applied thereto. This means that while the first elastic member 32 is accommodated in the accommodation part 34, in other words while the operation part 10 is positioned between the first elastic member 32 and the base end part 31*b*, the loop feed/return part 31 is able to move forwards and backwards.

Moreover, a guide (a groove into which the loop feed/return part 31 fits, for example) for moving the loop feed/return part 31 forwards and backwards in a straight line may be formed inside the housing 50.

Moreover, forwards movement of the loop feed/return part 31 may be regulated by the tip end part 31a abutting the support part 53. Furthermore, if a thick-walled part 54a is also provided on the loop feed/return mechanism 30 side, forwards movement of the loop feed/return part 31 may be regulated by the tip end part 31a of the loop feed/return part 31 abutting the inner wall surface 54b rather than the support part 53.

The suture thread feed mechanism 40 operates in conjunction with movement of the operation part 10 in order to feed out, from the tip end (blade edge) of the suture thread introduction needle 70, suture thread (suture thread 1 shown in FIGS. 1 to 3) which is movably inserted into the suture thread introduction needle 70. The suture thread feed mechanism 40 comprises the first hollow member 41, the second hollow member 42, the third hollow member 43, a suture thread clamping member 44, the suture thread feed part 45, a second elastic member 46, and the movement regulating member 47.

The first hollow member 41 has a hollow shape and is fixed to the base end side of the housing 50. The second hollow member 42 has a hollow shape and can move forwards and backwards inside the housing 50 in response to movement of the operation part 10. The third hollow member 43 has a hollow shape and is fixed to the tip end side of the housing 50. The suture thread 1 is inserted from outside the housing 50 into the first hollow member 41, second hollow member 42 and third hollow member 43. The third hollow member 43 in particular functions as a means for preventing flexing of the suture thread 1. However, the third hollow member 43 may be omitted so that the suture thread 1 is exposed inside the housing 50.

The second hollow member 42 has a larger inner diameter than the outer diameter of the first hollow member 41, and a smaller outer diameter than the inner diameter of the third hollow member 43. The second hollow member 42 can then move forwards and backwards when the tip end thereof is inserted into the hollow part of the third hollow member 43. Furthermore, the second hollow member 42 is designed to have the first hollow member 41 inserted into the hollow part at the base end side thereof, depending on the position of the second hollow member 42. In addition, the axial lengths of the first hollow member 41, second hollow member 42 and third hollow member 43 are determined in consideration of the size of the housing 50 and the length of the suture thread 1 which is to be projected from the tip end of the suture thread introduction needle 70, and there is no particular limitation to these lengths.

The movement regulating member 47 is fixed to the outer periphery on the base end side of the second hollow member 42. The movement regulating member 47 regulates the forwards and backwards movement of the second hollow member 42. That is, the second hollow member 42 moves forwards and backwards between abutment of the movement regulating member 47 with the stopper 51a and the stopper 51b formed on the inner wall surface of the housing 50. In accordance with this embodiment, the example described relates to a case in which the forwards movement of the second hollow member 42 is regulated by the movement regulating member 47 abutting the stopper 51a. Furthermore, according to this embodiment, a description will be given below of an exemplary case in which the backwards movement of the second hollow member 42 is regulated by the movement regulating member 47 abutting the stopper 51b.

Moreover, the forwards movement of the second hollow member 42 may be regulated by the tip end of the second hollow member 42 abutting the support part 52. Furthermore, if the third hollow member 43 is not provided, the forwards movement of the second hollow member 42 may be regulated by the tip end of the second hollow member 42 abutting the inner wall surface 54b. In addition, if the forwards movement of the second hollow member 42 is halted by part of the inner wall of the third hollow member 43, a tapered shape should be formed so that the inner diameter of the third hollow member 43 contracts towards the tip end, or a protrusion or the like should be formed in the cavity of the third hollow member 43.

Likewise, if the backwards movement of the second hollow member 42 is halted by part of the outer wall of the first hollow member 41, a tapered shape should be formed so that the outer diameter of the first hollow member 41 expands towards the base end, or a protrusion or the like should be formed on the outer periphery of the first hollow member 41. Furthermore, if the backwards movement of the second hollow member 42 is halted by the tip end of the second hollow member 42 being stopped by the base end (inner side) of the third hollow member 43, the tip end of the second hollow member 42 should project radially outwards and the base end of the third hollow member 43 should project radially inwards, and the projections should be formed in such a way as to be able to engage.

However, if the forwards movement of the second hollow member 42 is regulated by the outer peripheral surface at the tip end side of the second hollow member 42 coming into abutment with part of the inner wall of the third hollow member 43, the movement regulating member 47 regulates only the backwards movement of the second hollow member 42.

Furthermore, if the backwards movement of the second hollow member 42 is regulated by the inner peripheral surface at the base end side of the second hollow member 42 coming into abutment with the outer wall of the first hollow member 41, or by the tip end of the second hollow member 42 coming into abutment with the base end (inner side) of the third hollow member 43, the movement regulating member 47 regulates only the forwards movement of the second hollow member 42. In other words, the movement regulating member 47 is not an essential component, and the decision as to whether it is provided depends on the configuration of the first hollow member 41, second hollow member 42, third hollow member 43, stopper 51a and stopper 51b.

Furthermore, the first hollow member 41, second hollow member 42 and third hollow member 43 allow the suture thread 1 to pass therethrough, so the inner diameters thereof are set so that the suture thread 1 is able to pass therethrough. Furthermore, the first hollow member 41 and the second hollow member 42 are able to pass through the suture thread clamping member 44 which will be described later. The outer diameters of the first hollow member 41 and the second hollow member 42 therefore have to be set to the extent that they can pass through the cut in the suture thread clamping member 44.

Moreover, it is equally possible to form a tapered portion in the through-hole formed at the base end side of the housing 50 on the suture thread feed mechanism 40 side, or to make the base end of the first hollow member 41 project outwards of the housing 50. This makes it possible to lighten the burden of inserting the suture thread 1. However, as shown in FIGS. 1 to 3, the base end of the first hollow member 41 does not have to project outwards of the housing 50. Furthermore, if the base end side of the first hollow member 41 is funnel-shaped (a shape in which the wall surface grows gradually larger in diameter towards the base end), this makes it easier to insert the suture thread 1. Furthermore, the first hollow member 41 may be long enough to reach the base end of the housing 50, and a funnel-shaped member having an inner cavity may be fitted to the base end of the first hollow member 41.

In addition, the first hollow member 41, second hollow member 42 and third hollow member 43 should be hollow inside and may, for example, comprise a hollow columnar member (cylindrical member) or a prismatic member (rectangular cylinder) or the like. Furthermore, a cut (or incision) may be formed in part of the first hollow member 41, second hollow member 42 and third hollow member 43 so that the hollow parts thereof can communicate with the outside.

In addition, the third hollow member 43 also has the function of guiding the forwards and backwards movement of the second hollow member 42. The axial length of the third hollow member 43 should therefore be determined not only taking account of the length of the suture thread 1 which is to be fed out from the tip end of the suture thread introduction needle 70, but also taking account of the length of the second hollow member 42. That is to say, the axial length of the third hollow member 43 still allows part of the second hollow member 42 to be positioned in the hollow part of the third hollow member 43 when the second hollow member 42 has moved as far as possible backwards.

The suture thread clamping member 44 is made of natural rubber or synthetic rubber, or a metal, etc., for example, and is formed with a cut which runs therethrough in the front-to-rear direction in the centre. The suture thread clamping member 44 is allowed to move forwards and backwards by means of the second hollow member 42. The suture thread clamping member 44 can clamp the first hollow member 41, suture thread 1 or second hollow member 42 in the cut thereof. That is, the suture thread clamping member 44 is designed to clamp any of the first hollow member 41, suture thread 1 and second hollow member 42 depending on the position thereof, which varies according to the movement of the operation part 10.

Furthermore, the suture thread clamping member 44 is moved forwards and backwards while it is accommodated in the suture thread feed part 45. The suture thread clamping member 44 can move forwards until the second abutment part 45*a* of the suture thread feed part 45 runs into the first abutment part 33 of the loop feed/return part 31, and can move backwards until the base end surface of the suture thread feed part 45 runs into the inner wall surface 57*b* at the base end side of the housing 50. The suture thread 1 is fed out as a result of being clamped by the suture thread clamping member 44. This means that the suture thread 1 is clamped and fed out by the suture thread clamping member 44 while the suture thread clamping member 44 is separated from the first hollow member 41 and is clamping the second hollow member 42.

The suture thread clamping member 44 may consist of an elastic element made of natural rubber or synthetic rubber etc., or a ring made of a relatively soft metal, such as copper, for example. If the suture thread clamping member 44 consists of an elastic element, the suture thread 1 can be clamped using the elastic force thereof. If the suture thread clamping member 44 consists of an element such as a metal ring, the suture thread 1 can be clamped by plastic deformation which occurs at the same time as the ring is separated from the first hollow member 41. Furthermore, the cut formed in the suture thread clamping member 44 does not have to be a simple cut, and includes a slit shape or a hole having a smaller inner diameter than the outer diameter of the suture thread 1, or similar.

The suture thread feed part 45 comprises: the second abutment part 45*a*, a side wall extension part 45*b*, a main body part 45*c* and a fitting part 45*d*, and it can move backwards and forwards inside the housing 50 in response to the movement of the operation part 10. It should be noted that the suture thread feed part 45 may, for example, comprise a hollow columnar member (cylindrical member) or a prismatic member (rectangular cylinder) or the like, and the fitting part 45*d* thereof should be formed in such a way that the suture thread clamping member 44 can be fitted therein. Moreover, a guide for moving the suture thread feed part 45 forwards and backwards in a straight line (a groove into which the suture thread feed part 45 can be fitted, for example) may be formed inside the housing 50. In this case, the guide which is formed should not produce any friction resistance with respect to the movement of the suture thread feed part 45.

The second abutment part 45*a* is provided at the tip end of the side wall extension part 45*b*, for example, and is formed in the shape of a protrusion which projects towards the loop feed/return mechanism 30. The tip end surface of the operation part 10 which has moved forwards abuts the base end surface of the second abutment part 45*a*, and the movement from the operation part 10 is transmitted thereto. The second abutment part 45*a* is then subjected to a forwards force and the suture thread feed part 45 moves forwards.

Forwards movement of the suture thread feed part 45 is regulated by abutment of the tip end surface of the main body part 45*c* of the suture thread feed part 45 with the movement regulating member 47 which has stopped moving due to abutment with the base end surface of the stopper 51*a*.

Meanwhile, backwards movement of the suture thread feed part 45 is produced by the tip end of the second abutment part 45*a* being pressed by the base end surface of the first abutment part 33 which is formed on the loop feed/return part 31, and this movement is regulated by the base end surface of the suture thread feed part 45 abutting the inner wall surface 57*b*. However, the suture thread feed part 45 can automatically move backwards due to the resilience of the second elastic member 46 which will be described later. It should be noted that the shape of the second abutment part 45*a* is not limited to a protrusion, it simply needs to be a shape which can abut the first abutment part 33 and the operation part 10. Furthermore, the forwards and backwards movement of the second abutment part 45*a* is guided by the groove 22 which guides the movement of the operation part 10.

The side wall extension part 45*b* is an extension of part of the outer wall of the main body part 45*c* towards the tip end. The side wall extension part 45*b* is positioned on the loop feed/return mechanism 30 side. Moreover, there is no particular limitation as to the axial length of the side wall extension part 45*b*, but it is determined to take account of the size of the housing 50 and the length of the suture thread 1 to be fed out from the tip end of the suture thread introduction needle 70. Furthermore, there is no particular limitation as to the thickness of the side wall extension part 45*b*, but it should be strong enough to withstand the force applied by the second abutment part 45*a*.

The main body part 45*c* has the fitting part 45*d* formed therein, and is also formed with a through-hole which allows the suture thread 1 to pass through backwards and forwards, by way of the fitting part 45*d*. The main body part 45*c* is disposed inside the housing 50 in such a way as to be able to move backwards and forwards. As described above, if a guide for moving the suture thread feed part 45 forwards and backwards in a straight line is formed inside the housing 50, the main body part 45*c* may be disposed on this guide. Furthermore, the suture thread feed part 45 is moved backwards until the base end surface of the main body part 45*c* abuts the inner wall surface 57*b* of the housing 50.

The fitting part 45*d* is formed in the main body part 45*c* and allows the suture thread clamping member 44 to be fitted therein. The movement of the suture thread clamping member 44 is restricted when it is fitted into the fitting part 45*d*. It should be noted that there is no particular limitation to the size of the fitting part 45*d* provided that it has a size which allows the suture thread clamping member 44 to be fitted therein.

The second elastic member 46 consists of an elastic member which is extendible in the front-to-rear direction (for instance, a spring (coil spring, air spring etc.) or a rubber element). The second elastic member 46 is disposed between the inner wall surface 54*b* and the movement regulating member 47 which is fixed to the second hollow member 42, and extends and contracts between the inner wall surface 54*b* and the movement regulating member 47. The second elastic member 46 causes the suture thread feed part 45 to move backwards by pressing the movement regulating member 47 using the resilience thereof. If the second elastic member 46 consists of a spring, the second elastic member 46 should be disposed in such a way as to wind around the outer periphery of the third hollow member 43 and the second hollow member 42.

The loop introduction needle 60 has a lumen and accommodates the loop forming part 80 in said lumen in such a way that it can move forwards and backwards. When the loop introduction needle 60 is fitted to the housing 50 the base end thereof opens inside the housing 50 in order to allow communication with the inside of the housing 50. The loop introduction needle 60 is fitted to the tip end of the housing 50 in such a way that the axial centre thereof is aligned with the axial centre of the loop feed/return mechanism 30. If the loop introduction needle 60 is fitted to the housing 50 in this way, the loop forming part 80 can be fed out and returned in a straight line. The loop introduction needle 60 should be made of a metal such as stainless steel, for example.

Furthermore, the loop introduction needle 60 has a cutting surface, at the tip end, for piercing the skin. The cutting surface may be formed by cutting the loop introduction needle 60 on a plane which obliquely intersects the axial centre thereof. The tip end opening of the loop introduction needle 60 should be oriented towards the suture thread introduction needle 70 so that the loop 82 of the loop forming part 80 extends in the direction of the suture thread introduction needle 70 in a reliable manner, as will be described later. It should be noted that the tip end side of the loop introduction needle 60 does not mean only the very tip of the loop introduction needle 60, it also includes the side surfaces in the tip-end region of the loop introduction needle 60.

Moreover, there is no particular limitation as to the shape of the loop introduction needle 60 provided that it can pierce the skin and allows the loop forming part 80 to be inserted therein. For example, a needle of outer diameter around 21-17 G (preferably 20-18 G) and length around 70-120 mm (preferably 80-100 mm) may be used as the loop introduction needle 60. Furthermore, a bevelled part may be formed at the tip end of the loop introduction needle 60 so as not to cut the suture thread 1 when it is gripped. In addition, it should be possible to adjust the position of the tip end of the loop introduction needle 60 (the position relative to the suture thread 1 which has been fed out) through the position of the support part 52.

The suture thread introduction needle 70 has a lumen in which the suture thread 1 is inserted in such a way as to be able to move forwards and backwards. The base end of the suture thread introduction needle 70 communicates with the hollow part of the third hollow member 43 when the suture thread introduction needle 70 is fitted to the housing 50. The suture thread introduction needle 70 is fitted to the tip end of the housing 50 in such a way that the axial centre thereof is aligned with the axial centre of the suture thread feed mechanism 40. If the suture thread introduction needle 70 is fitted to the housing 50 in this way, the suture thread 1 can be fed out in a straight line. The suture thread introduction needle 70 may be formed from a metal such as stainless steel, for example. Moreover, the base end of the suture thread introduction needle 70 may function as the third hollow member 43.

Furthermore, the suture thread introduction needle 70 has a cutting surface, at the tip end, for piercing the skin. The cutting surface may be formed by cutting the suture thread introduction needle 70 on a plane which obliquely intersects the axial centre thereof. There is no particular limitation as to the orientation of the tip end opening of the suture thread introduction needle 70, but it preferably faces the direction of the loop introduction needle 60. It should be noted that the tip end side of the suture thread introduction needle 70 does not mean only the very tip of the suture thread introduction needle 70, it also includes the side surfaces in the tip-end region of the suture thread introduction needle 70.

Moreover, there is no particular limitation as to the shape of the suture thread introduction needle 70 provided that it can pierce the skin and allows the suture thread 1 to be inserted therein. For example, a needle of outer diameter around 21-17 G (preferably 20-18 G) and length around 70-120 mm (preferably 80-100 mm) may be used as the suture thread introduction needle 70. Furthermore, it should be possible to adjust the position of the tip end of the loop introduction needle 60 (the position relative to the loop 82 which has been fed out) through the position of the support part 53.

As described above, the loop introduction needle 60 and the suture thread introduction needle 70 are supported in parallel a prescribed distance apart at the tip end of the housing 50. The distance between the loop introduction needle 60 and the suture thread introduction needle 70 should be set at the length over which the patient's abdominal wall and internal organ wall are to be fixed by the suture thread 1 (around 10-30 mm, for example). The patient's abdominal wall and internal organ wall can be properly fixed by the suture thread 1 if the distance between the loop introduction needle 60 and the suture thread introduction needle 70 is within this range.

The loop forming part 80 is inserted into the loop introduction needle 60 in such a way as to be able to move forwards and backwards. The loop forming part 80 comprises: the base end fixing part 83 which is fixed to the tip end of the loop feed/return part 31; the loop 82 which is fixed to the tip end; and a rod-like shaft 81 which has a smaller outer diameter than the inner diameter of the loop introduction needle 60 and connects the base end fixing part 83 and the loop 82. The loop 82 is made of an elastic material and it reverts to an annular shape when it has been fed out from the tip end of the loop introduction needle 60 (when no external force is applied thereto), and changes to a substantially linear shape which can be accommodated inside the loop introduction needle 60 when it has not been fed out from the tip end of the loop introduction needle 60.

When the loop 82 has been fed out from the tip end of the loop introduction needle 60, it extends in the direction of the suture thread introduction needle 70 in such a way that the suture thread 1 which is fed out from the tip end of the suture thread introduction needle 70 passes through the inside of the loop 82. For example, the loop 82 may be fixed to the tip end of the rod-like shaft 81 at a prescribed angle so as to form a curved shape when it has been fed out from the tip end of the loop introduction needle 60. This curved shape may be such that when the loop 82 is seen from the side the top part of the curved section projects forwards, for example. If the loop 82 is formed with this kind of shape, the suture thread 1 can be positioned inside the loop 82 with greater certainty. Furthermore, if the centre of the loop 82 lies over the extension of the suture thread introduction needle 70, then when the suture thread 1 extends straight forwards, said suture thread 1 can be positioned inside the loop 82 with greater certainty.

Furthermore, although there is no particular limitation to the tip end shape of the loop 82, it may be substantially V-shaped or substantially U-shaped with the tip end at the centre in order to narrow the distance between the sections which grip the suture thread 1 (the substantially V-shaped or substantially U-shaped portion). If this kind of shape is adopted, the suture thread 1 which has been fed out from the tip end of the suture thread introduction needle 70 can be gripped more securely. The loop 82 may consist of a deformable member, for example: stainless steel wire (high tensile stainless steel for springs); piano wire (nickel-plated or chromium-plated piano wire); or superelastic alloy wire (titanium-nickel alloy, copper-zinc alloy (or an alloy containing beryllium, silicon, tin, aluminium or gallium etc. therewith), nickel-aluminium alloy etc.).

The rod-like shaft 81 may be constructed using, among other things, a metal (e.g. stainless steel) or a synthetic resin (e.g. a polyolefin such as polypropylene or polyethylene, or a fluororesin such as PTFE or ETFE). A stylet or the like may be used for the rod-like shaft 81. Furthermore, provided that the base end fixing part 83 is fixed to the tip end of the loop feed/return part 31, there is no particular limitation to the method of fixing the base end fixing part 83. For example, the base end fixing part 83 may be fixed using adhesive or the like, or a notch etc. may be provided at the tip end of the loop feed/return part 31 and the base end fixing part 83 may be fixed thereto by fitting into said notch etc. Moreover, when the loop 82 is made of a relatively rigid material, the rod-like shaft 81 and the loop 82 may be made of the same material. If that is the case, the rod-like shaft 81 and the loop 82 may be formed as a single element or as separate elements.

In the suturing instrument 100, the operation part 10 and the loop feed/return mechanism 30 and suture thread feed mechanism 40 are not linked. The loop feed/return mechanism 30 and the suture thread feed mechanism 40 are not linked either. That is to say, the operation part 10, loop feed/return mechanism 30 and suture thread feed mechanism 40 are independent of one another. Nonetheless, a simple operation of the suturing instrument 100 makes it possible to provide a time delay between the timing for feeding out the loop 82 and the timing for feeding out the suture thread 1, without requiring excessive work by the practitioner for operation, and a situation can be achieved in which the suture thread 1 passes through the internal organ wall and the abdominal wall. The procedure for achieving this will be described in detail.

The practitioner first of all inserts the suture thread 1 into the first hollow member 41 of the suture thread feed mechanism 40 as a preliminary operation of the suturing instrument 100. Here, the practitioner feeds the suture thread 1 into the suture thread introduction needle 70 to a length such that the suture thread 1 does not project from tip end of the suture thread introduction needle 70. When the operation part 10 is moved forwards after the suturing instrument 100 has been made to pierce into the internal organ, the forwards movement of the operation part 10 is first of all transmitted to the loop feed/return mechanism 30, and is then transmitted to the suture thread feed mechanism 40. It should be noted that the practitioner may make use of an assembly in which the suture thread 1 is already set in the suturing instrument 100.

In the initial state (or the state prior to the second and subsequent operations) in which the operation part 10 is not being operated, the situation on the loop feed/return mechanism 30 side is that the base end part 31*b* of the loop feed/return part 31 is abutting the inner wall surface 57*a* of the housing 50. Here, the first elastic member 32 which is being compressed by a prescribed force is accommodated inside the accommodation part 34. Furthermore, the operation part 10 is held between the first elastic member 32 and the base end part 31*b* of the loop feed/return part 31.

When the practitioner moves the operation part 10 forwards, this force is transmitted to the first elastic member 32. The first elastic member 32 is compressed by a prescribed force, so the tip end part 31*a* of the loop feed/return part 31 is pushed by the tip end of the first elastic member 32. That is, the operation part 10, loop feed/return part 31 and first elastic member 32 move forwards while the respective positions thereof are maintained. When this happens, the loop forming part 80 fixed to the tip end part 31*a* of the loop feed/return part 31 also moves forwards, and the loop 82 positioned at the tip end of the loop forming part 80 juts out from the tip end of the loop introduction needle 60, and opens into an annular shape.

When the operation part 10 is moved further forwards, the first abutment part 33 of the loop feed/return part 31 runs into the inner wall surface 54*b*. In this state, when a force greater than the force being applied to the first elastic member 32 is transmitted to the first elastic member 32 by way of the operation part 10, the first elastic member 32 is further compressed. That is, the loop 82 which has been fed out from the tip end of the loop introduction needle 60 can be maintained in an open state. By virtue of this configuration, it is possible to adjust the timing for feeding out the suture thread 1 and the timing for feeding out the loop 82, for instance delaying the timing for feeding out the suture thread 1 with respect to the timing for feeding out the loop 82. In other words, the annular shape of the loop 82 can be maintained as the operation part 10 continues to move forwards.

Next, when the operation part 10 is no longer being operated towards the tip end, the compressive force acting on the first elastic member 32 is released, and the loop feed/return part 31 starts to move backwards. That is, the operation part 10 moves backwards under the resilience of the first elastic member 32 until it abuts the base end part 31*b* of the loop feed/return part 31. When the practitioner then moves the operation part 10 further backwards, the rearward force of the operation part 10 which is abutting the base end part 31*b* of the loop feed/return part 31 is transmitted to the loop feed/return part 31. As a result, the base end part 31b of the loop feed/return part 31 is pushed backwards and the loop feed/return part 31 moves backwards.

A separate elastic element such as a spring or a rubber element may be provided in addition to the first elastic element 32, and the operation part 10 may be moved backwards using the resilience of this elastic element. When this kind of elastic element is provided, the operation to move the operation part 10 backwards is simplified, and the work of the practitioner can be lightened. That is, the suture thread 1 can be inserted through the internal organ wall and the abdominal wall essentially by means of a one-touch operation, without the practitioner having to perform a return operation, as will be described later.

When the loop feed/return part 31 moves backwards, the loop 82 also starts to move backwards. At this point, the suture thread 1 which has been fed out from the tip end of the suture thread introduction needle 70 has passed through the loop 82. When the loop 82 starts to move backwards, the annular shape of the loop 82 therefore becomes gradually smaller, and the suture thread 1 is gripped by the loop 82. As the loop 82 moves further backwards, the suture thread 1 is gripped at the tip end of the loop introduction needle 60.

In the initial state (or the state prior to the second and subsequent operations) in which the operation part 10 is not being operated, the situation on the suture thread feed mechanism 40 side is that the suture thread clamping member 44 has over-mounted the first hollow member 41, which is to say that the first hollow member 41 is clamped, so the suture thread 1 is not held by the suture thread clamping member 44 and is in a free state of mobility (a state in which the suture thread 1 is not clamped by the suture thread clamping member 44 and can be freely advanced and retracted).

Even if the practitioner moves the operation part 10 forwards, operation does not start straight away on the suture thread feed mechanism 40 side. In addition, the suture thread feed part 45 starts to move forwards when the operation part 10 is moved forwards and abuts the second abutment part 45a. That is, the movement of the operation part 10 is transmitted to the components of the suture thread feed mechanism 40 by way of the second abutment part 45a.

When the suture thread feed part 45 moves forwards, the suture thread clamping member 44 also moves forward in tandem. When the suture thread clamping member 44 moves by a prescribed distance, the first hollow member 41 is withdrawn from the suture thread clamping member 44. The suture thread 1 is then in a state in which it is running through the cut in the suture thread clamping member 44, in other words a state in which the suture thread clamping member 44 is clamping the suture thread 1. In this state, the clamping force of the suture thread clamping member 44 is transmitted to the suture thread 1 and the suture thread 1 is gripped by the suture thread clamping member 44.

At this point, the base end of the second hollow member 42 is in contact with the tip end of the suture thread clamping member 44. The movement of the operation part 10 is then transmitted to the second hollow member 42 by way of the suture thread clamping member 44, and the second hollow member 42 also moves forwards as it is pushed by the suture thread clamping member 44. Moreover, the forwards movement of the second hollow member 42 causes the second elastic member 46 to be pushed by the movement regulating member 47, so the second elastic member 46 is compressed in the forwards direction.

The suture thread 1 is gripped by the suture thread clamping member 44 and is therefore fed out from the tip end of the suture thread introduction needle 70 together with the forwards movement of the second hollow member 42. That is to say, the suture thread 1 is fed out from the tip end of the suture thread introduction needle 70 at a delayed timing with respect to the timing at which the loop 82 is fed out from the tip end of the loop introduction needle 60. This means that it is possible to provide a time delay between the timing for feeding out the loop 82 and the timing for feeding out the suture thread 1, and the suture thread 1 can be easily inserted into the loop 82. Moreover, the suturing instrument 100 makes it possible to freely adjust the timing for feeding out the suture thread 1 and the timing for feeding out the loop 82.

When the operation part 10 is moved further forwards, the movement regulating member 47 runs into the stopper 51a. When this occurs, the forwards movement of the suture thread feed part 45 together with the second hollow member 42 is stopped. In this state, a greater force than the force which is being applied to the first elastic member 32 is transmitted to the first elastic member 32 by way of the operation part 10, and when the operation part 10 is moved further forwards, the suture thread feed part 45 moves forwards whereby the base end of the second hollow member 42 penetrates the suture thread clamping member 44. When this occurs, the clamping of the suture thread 1 by the suture thread clamping member 44 is released and the suture thread 1 is in a free state. That is, the suture thread 1 does not move forwards. It should be noted that an exemplary case is described here in which the forwards movement of the second hollow member 42 is regulated by the movement regulating member 47 running into the stopper 51a, but this is not limiting, as described above.

Next, when operation of the operation part 10 towards the tip end is halted, the compressive force acting on the second elastic member 46 is released and the suture thread feed part 45 moves backwards as far as the position where the movement regulating member 47 runs into the stopper 51b. However, the second hollow member 42 remains penetrating the suture thread clamping member 44. It should be noted that in this case the backwards movement of the second hollow member 42 is regulated by the movement regulating member 47 running into the stopper 51b, but this is not limiting, as described above.

When the operation part 10 is moved further backwards while the movement regulating member 47 is in abutment with the stopper 51b, the base end surface of the first abutment part 33 of the loop feed/return part 31 abuts the tip end surface of the second abutment part 45a of the suture thread feed part 45, and the force of the operation part 10 is transmitted to the suture thread feed part 45 by way of the loop feed/return part 31. The movement of the second hollow member 42 is stopped by the stopper 51b, and therefore only the suture thread feed part 45 moves backwards. The second hollow member 42 is withdrawn from the cut in the suture thread clamping member 44, which then clamps the first hollow member 41. That is to say, the clamping force of the suture thread clamping member 44 stops being applied to the second hollow member 42 and is applied to the first hollow member 41.

As will be described later, with the suturing instrument 100, the feeling of the suture thread 1 being gripped at the tip end of the loop introduction needle 60 is directly transmitted to the practitioner, so when the suture thread 1 is gripped at the tip end of the loop introduction needle 60, the components (operation part 10, loop feed/return mechanism 30 and suture thread feed mechanism 40) have not yet returned to their initial state. That is to say, while the suture thread 1 is being gripped by the loop introduction needle 60, the loop forming part 80 cannot enter the loop introduction needle 60 and the loop feed/return part 31 cannot move any further backwards.

When the loop introduction needle 60 and suture thread introduction needle 70 of the suturing instrument 100 are withdrawn from inside the internal organ to the abdominal wall side while the suture thread 1 is being gripped at the tip end of the loop introduction needle 60, the suture thread 1 is smoothly guided because it is free, and the suture thread 1 assumes a state of having passed through the internal organ wall and the abdominal wall in substantially a U-shape. Next, the suture thread 1 is cut using the cutting surface of the suture thread introduction needle 70 which has been withdrawn to outside the body, or another cutting means (scissors, cutter etc.). The excess suture thread 1 gripped at the tip end of the loop introduction needle 60 is then removed. When this is done, the loop forming part 80 is able to enter the loop introduction needle 60, and the loop feed/return part 31 can move backwards. In this state, if the operation part 10 is moved further backwards, the first abutment part 33 and second abutment part 45a come into abutment, and each component returns to the same position as in the initial state. Accordingly, the same state as the initial state is reached, in which the suture thread 1 is inserted up to the tip end of the suture thread introduction needle 70, and therefore the internal organ wall can be fixed any number of times using the above procedure. Moreover, if the suture thread 1 is projecting further towards the tip end than the cutting edge of the suture thread introduction needle 70 after the suture thread 1 has been cut, the same state as the initial state may be set by pulling the suture thread 1 towards the base end by hand.

However, the first abutment part 33 and second abutment part 45a may be brought into abutment at the same time as the suture thread 1 is gripped at the tip end of the loop introduction needle 60.

By virtue of the suturing instrument 100, the forwards movement of the operation part 10 can be transmitted to the loop 82 at an earlier stage, and after this the forwards movement of the operation part 10 can be transmitted to the suture thread 1, so the timing for feeding out the suture thread 1 can be delayed with respect to the timing for feeding out the loop 82. As a result, the suture thread 1 can be reliably inserted into the loop 82 and the suture thread 1 can be securely gripped.

To be specific, when the operation part 10 is moved towards the tip end, the loop feed/return mechanism 30 starts to act first of all and only the loop 82 is fed out at an early stage using the elastic force of the first elastic member 32. Then, when the loop 82 has been completely fed out, the movement of the operation part 10 is transmitted only to the first elastic member 32 on the loop feed/return mechanism 30 side, in such a way that the annular shape of the loop 82 is maintained as the suture thread 1 is fed out, and the shape of the loop 82 can be maintained. However, the timing for feeding out the suture thread 1 and the timing for feeding out the loop 82 can be adjusted so that the suture thread 1 may be fed out without the loop 82 being completely fed out. Furthermore, the suture thread 1 and loop 82 may be fed out at the same time.

Meanwhile, the suture thread feed mechanism 40 starts operating at a later stage than the operation of the loop feed/return mechanism 30. Immediately after the start of movement, the suture thread feed mechanism 40 leaves the suture thread 1 free, adopting a state in which the suture thread clamping member 44 over-mounts the first hollow member 41. On the suture thread feed mechanism 40 side, the suture thread clamping member 44 then clamps the suture thread 1 by withdrawing from the first hollow member 41, and the movement of the operation part 10 is transmitted to the suture thread 1.

In this way, the suturing instrument 100 makes it possible to provide a time delay between the timing for feeding out the loop 82 and the timing for feeding out the suture thread 1. Specifically, the suturing instrument 100 allows the suture thread 1 to be fed out once the loop 82 has already been fed out, so the suture thread 1 is readily inserted into the loop 82 which is formed into an annular shape. This means that the suturing instrument 100 makes it possible to alter and correct the timing for feeding out the suture thread 1 and the timing for feeding out the loop 82 by adjusting the lengths of the loop feed/return part 31, first hollow member 41 and second hollow member 42, and the positions of the stopper 51a and stopper 51b.

Shortly after the loop feed/return part 31 has been moved backwards, the first abutment part 33 of the loop feed/return part 31 abuts the second abutment part 45a of the suture thread feed part 45. When the first abutment part 33 of the loop feed/return part 31 comes into abutment with the second abutment part 45a of the suture thread feed part 45, the feeling of this abutment is transmitted to the practitioner by way of the operation part 10. If the suture thread 1 is gripped by the loop 82 after the first abutment part 33 of the loop feed/return part 31 has come into abutment with the second abutment part 45a of the suture thread feed part 45, it is difficult to judge whether the suture thread 1 is being gripped by the loop 82. If the suture thread 1 is gripped by the loop 82 before the first abutment part 33 of the loop feed/return part 31 comes into abutment with the second abutment part 45a of the suture thread feed part 45, it is a simple matter to judge the state of gripping of the suture thread 1 by the loop 82, and the ease of use for the practitioner is further improved.

With the suturing instrument 100, the base end surface of the first abutment part 33 and the tip end surface of the second abutment part 45a are designed to come into abutment after the suture thread 1 has been gripped at the tip end of the loop introduction needle 60 or at the same time as the suture thread 1 is gripped at the tip end of the loop introduction needle 60. As a result, the feeling of the suture thread 1 being gripped at the tip end of the loop introduction needle 60 is transmitted directly to the practitioner through the operation part 10. Moreover, the timing at which the base end surface of the first abutment part 33 and the tip end surface of the second abutment part 45a come into abutment should be at the same time as the suture thread 1 is gripped at the tip end of the loop introduction needle 60 or after the suture thread 1 has been gripped at the tip end of the loop introduction needle 60. It is therefore a simple matter for the practitioner to judge that the suture thread 1 has been gripped at the tip end of the loop introduction needle 60, and the ease of use is further improved.

The suturing instrument 100 is formed with a clearance such that the base end surface of the first abutment part 33 and the tip end surface of the second abutment part 45a do not come into abutment when the suture thread 1 is gripped at the tip end of the loop introduction needle 60. Furthermore, the suturing instrument 100 is such that the base end surface of the first abutment part 33 and the tip end surface of the second abutment part 45a come into abutment when the suture thread 1 is gripped at the tip end of the loop introduction needle 60. That is to say, by adjusting the distance between the base end surface of the first abutment part 33 and the tip end surface of the second abutment part 45a, it is possible to adjust the timing when the suture thread 1 is gripped at the tip end of the loop introduction needle 60 and the timing of abutment between the base end surface of the first abutment part 33 and the tip end surface of the second abutment part 45a. As a result, the timing of abutment between the base end surface of the first abutment part 33 and the tip end surface of the second abutment part 45a can be delayed with respect to the timing when the suture thread 1 is gripped at the tip end of the loop introduction needle 60, or can be synchronized with the timing when the suture thread 1 is gripped at the tip end of the loop introduction needle 60.

Moreover, when the timing of abutment between the base end surface of the first abutment part 33 and the tip end surface of the second abutment part 45a can be delayed with respect to the timing when the suture thread 1 is gripped at the tip end of the loop introduction needle 60, a clearance should be formed between the base end surface of the first abutment part 33 and the tip end surface of the second abutment part 45a when the suture thread 1 is gripped at the tip end of the loop introduction needle 60, and this clearance is not limited to a prescribed value. For example, the clearance should be adjusted to a value such that the base end surface of the first abutment part 33 and the tip end surface of the second abutment part 45a do not come into abutment at least until the tip end of the loop 82 is substantially coincident with the tip end of the loop introduction needle 60.

Figure 4:
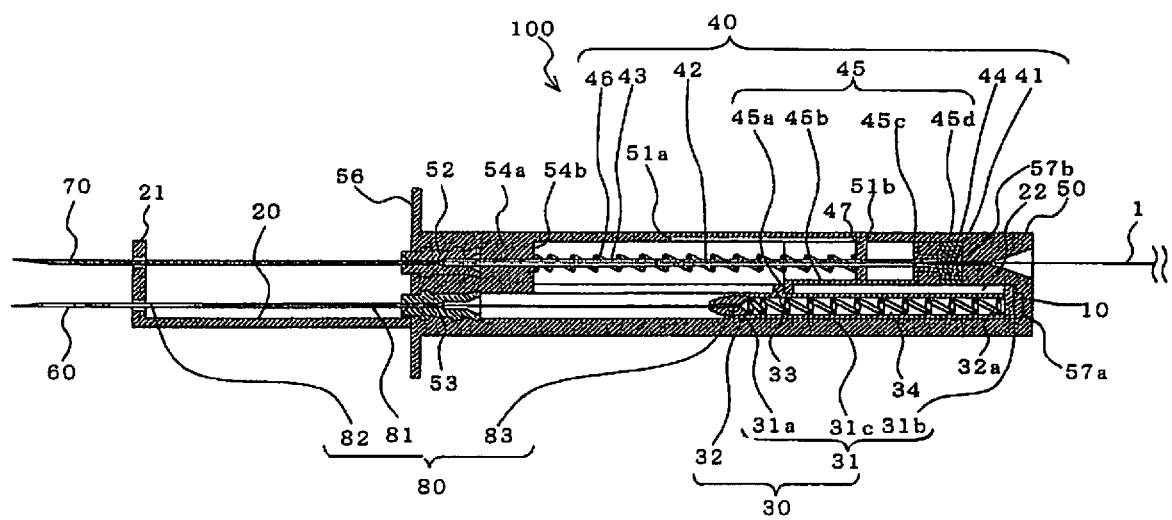
FIG. 4 is a schematic view in cross section showing, in simplified form, the procedure for operating the medical suturing instrument according to one or more embodiments of the invention.

FIGS. 4 to 7 are schematic views in cross section showing, in simplified form, the operating procedure for the suturing instrument 100. The specific operating procedure for the suturing instrument 100 will be described with reference to FIGS. 4 to 7C. FIG. 4 shows the piercing operation of the suturing instrument 100; FIGS. 5A-5C and 6A-6C show the forwards movement operations of each component, referred to below as "pushing operations." In particular, FIGS. 5A-5C show: pushing operation 1 (B1) in FIG. 5A, pushing operation 2 (B2) in FIG. 5B, and pushing operation 3 (B3) in FIG. 5C); FIGS. 6A-6C show: pushing operation 4 (B4) in FIG. 6A, pushing operation 5 (B5) in FIG. 6B, and pushing operation 6 (B6) in FIG. 6C); and FIGS. 7A-7C shows the backwards movement operations of each component (referred to below as "return operations" (return operation 1 (C1) in FIG. 7A, return operation 2 (C2) in FIG. 7B, and return operation 3 (C3) in FIG. 7C). Furthermore, FIGS. 5A to 7C also show diagrams highlighting the fed out state of the suture thread 1 and the loop 82. It should be noted that in FIGS. 5A to 7C, the reference symbols for the loop feed/return mechanism 30, loop feed/return part 31, suture thread feed mechanism 40, suture thread feed part 45 and loop forming part 80 have been omitted for convenience in order to make the state of movement of each component clearer. Furthermore, FIG. 4 also shows the return operation 4 (C4).

Referring to FIG. 4, the piercing operation for an initial state of the suturing instrument 100 and also including the state prior to the second and subsequent operations, for example, a return operation for (C4) is illustrated. The practitioner first of all pierces the patient's body using the suturing instrument 100 which is in a state such that the loop 82 of the loop forming part 80 is accommodated inside the loop introduction needle 60 and the suture thread 1 is accommodated inside the suture thread introduction needle 70. At this point, the suture thread 1 is inserted inside the suture thread introduction needle 70 in such a way as not to project from the tip end of the suture thread introduction needle 70. Furthermore, the suture thread clamping member 44 has over-mounted the first hollow member 41, and the suture thread 1 is free, in other words not moving forwards. In addition, the base end part 31b of the loop feed/return part 31 is in abutment with the inner wall surface 57a.

Figure 5A:
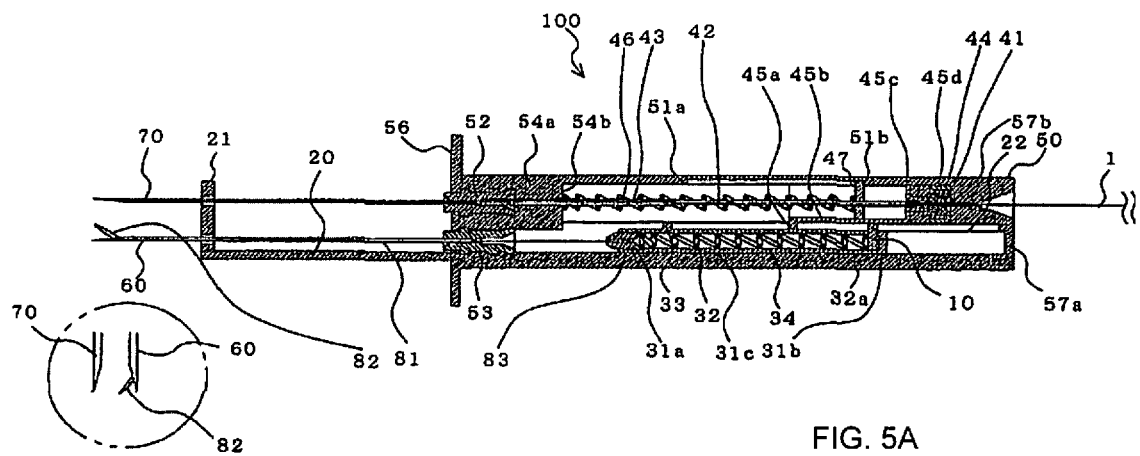
FIGS. 5A-5C illustrate a schematic view in cross section showing, in simplified form, the procedure for operating the medical suturing instrument according to one or more embodiments of the invention.

Referring now to FIG. 5A, the pushing operation 1 is illustrated from the start of feeding out of the loop 82. When a forwards force is applied to the operation part 10 by the practitioner, the loop feed/return part 31 starts to move forwards by way of the first elastic member 32. When the loop feed/return part 31 moves backwards and forwards, the loop forming part 80 also moves backwards and forwards. The loop feed/return part 31 is able to move forwards until the tip end part 31a runs into the support part 53.

The suture thread feed mechanism 40 does not move yet, even though the loop feed/return mechanism 30 has started moving. The suture thread clamping member 44 has over-mounted the first hollow part 41, and at this point the suture thread 1 remains free.

Figure 5B:
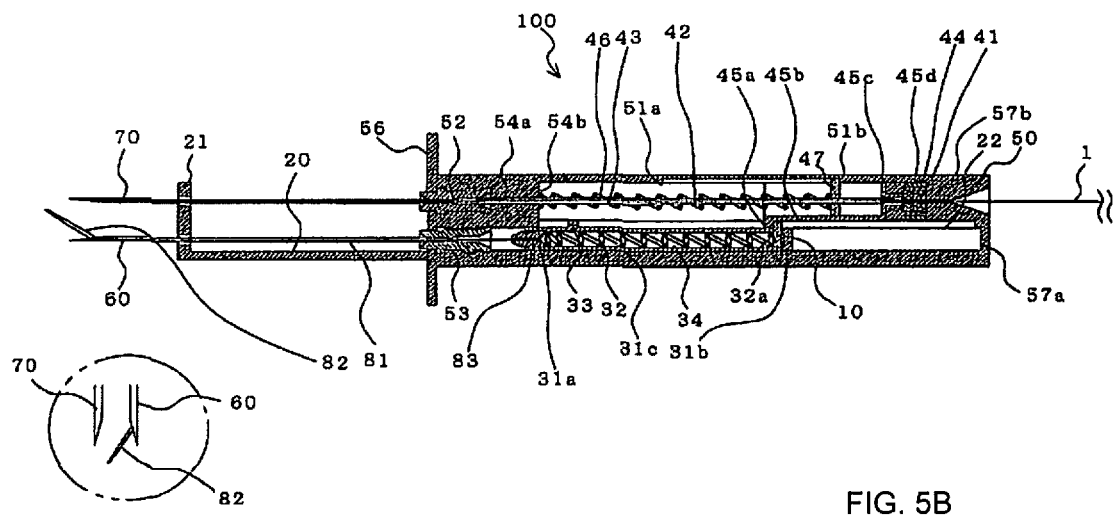

Referring now to FIG. 5B, the pushing operation 2 is illustrated at the start of the restoration of the loop 82. When the operation part 10 is moved further forwards by the practitioner, the loop forming part 80 which is connected to the tip end part 31a on the loop feed/return mechanism 30 side also moves towards the tip end inside the cavity of the loop introduction needle 60, and is fed out from the tip end of the loop introduction needle 60. When the loop 82 is fed out from the tip end of the loop introduction needle 60, no external force is applied thereto so its annular shape is restored.

In the suture thread feed mechanism 40, the operation part 10 abuts the second abutment part 45a of the suture thread feed mechanism 40 before the loop 82 has been fully restored.

Figure 5C:
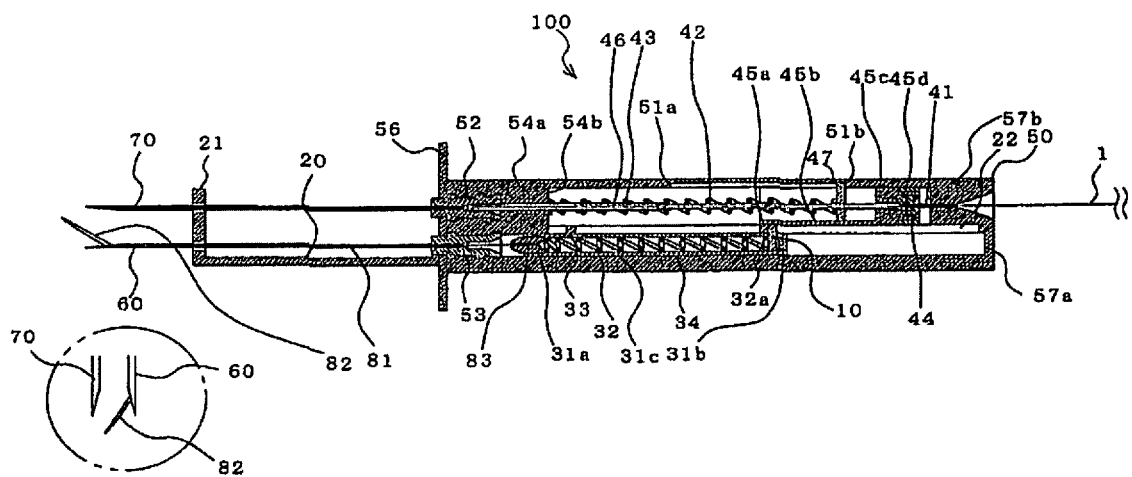

Referring now to FIG. 5C, the pushing operation 3 is illustrated at the start of the operation of the suture thread feed mechanism 40. The loop feed/return part 31 continues moving forwards until the first abutment part 33 abuts the inner wall surface 54b.

The suture thread feed mechanism 40 starts to move forwards when the operation part 10 comes into abutment with the second abutment part 45a of the suture thread feed mechanism 40. When the second abutment part 45a is pushed forwards by the operation part 10, the suture thread feed part 45 starts to move forwards. The suture thread clamping member 44 is fitted to the suture thread feed part 45, so the suture thread clamping member 44 starts to move forwards along the first hollow member 41 together with the suture thread feed part 45.

Figure 6A:
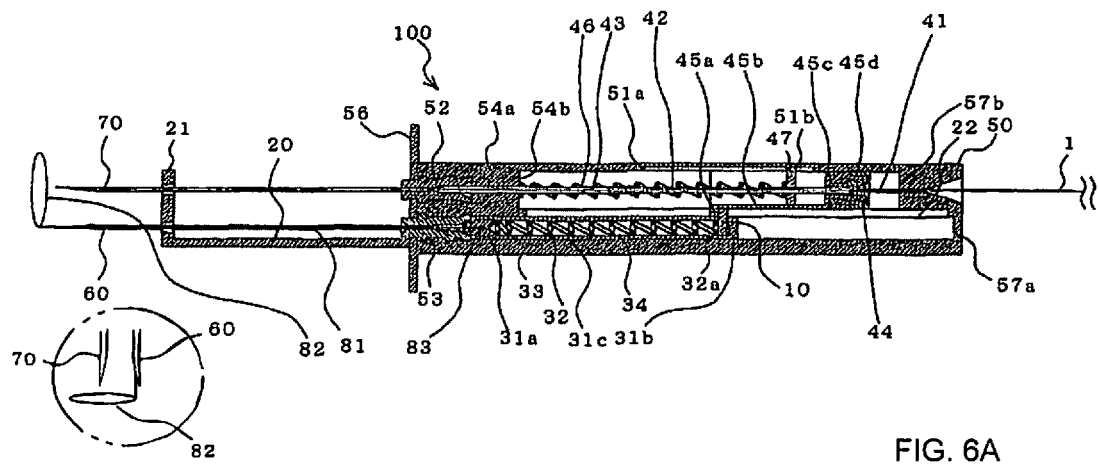
FIGS. 6A-6C illustrate a schematic view in cross section showing, in simplified form, the procedure for operating the medical suturing instrument according to one or more embodiments of the invention.

Referring now to FIG. 6A, the pushing operation 4 is illustrated in which the suture thread 1 is clamped by means of suture thread clamping member 44. When the operation part 10 is moved further forwards by the practitioner, on the loop feed/return mechanism 30 side, the first abutment part 33 abuts the inner wall surface 54b and the loop feed/return part 31 cannot move any further forwards. When this happens, the movement of the operation part 10 is transmitted only to the first elastic member 32, and the first elastic member 32 is compressed in the forwards direction inside the accommodation part 34 of the loop feed/return part 31. This means that only the first elastic member 32 moves forwards while the shape of the loop 82 is maintained. At this point, the action of the first elastic member 32 causes a load to be gradually exerted by way of the operation part 10 in the practitioner's hand. The operation part 10 can therefore move smoothly forwards.

When the first abutment part 33 abuts the inner wall surface 54b, the forwards movement of the loop feed/return part 31 is regulated, and only the first elastic member 32 moves forwards if the operation part 10 is moved further forwards. That is to say, the loop feed/return part 31 can compress only the first elastic member 32 towards the tip end, without moving any further towards the tip end. As a result, the shape of the loop 82 which has been fed out from the tip end of the loop introduction needle 60 is maintained.

On the suture thread feed mechanism 40 side, the forwards movement of the suture thread feed part 45 continues and the suture thread clamping member 44 separates from the first hollow member 41 to clamp the suture thread 1.

At the same time, the second hollow member 42 also continues to move forwards, so the second elastic member 46 starts to be compressed as the movement regulating member 47 moves forwards.

Figure 6B:
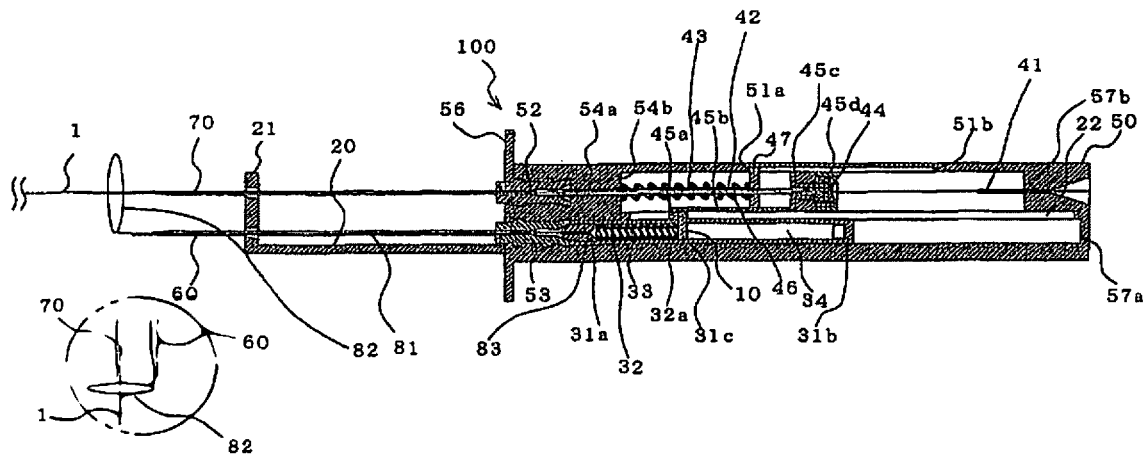

Referring now to FIG. 6B, the pushing operation 5 is illustrated in which a start of a feeding out the suture thread 1 occurs. In the loop feed/return mechanism 30, the movement of the operation part 10 is transmitted only to the first elastic member 32, and the first elastic member 32 continues to be compressed.

In the suture thread feed mechanism 40, if the suture thread clamping member 44 moves further forwards while the suture thread 1 is being clamped by the suture thread clamping member 44, the suture thread 1 which is being clamped by the suture thread clamping member 44 also starts to move forwards, and the suture thread 1 starts to be fed out from the tip end of the suture thread introduction needle 70. The suture thread 1 then passes through the loop 82 which has already been fed out. Moreover, the second hollow member 42 is also pushed forwards by the suture thread clamping member 44 and moves forwards.

After this, the suture thread feed part 45 continues moving forwards until the movement regulating member 47 runs into the stopper 51a. At this point, the required length of suture thread 1 has been fed out from the suture thread introduction needle 70.

In accordance with some embodiments, a position of the operation part at this point in the operation of the medical suturing instrument is referred to as a first position. According to these embodiments, with the operation part in the first position, the operation parts has moved the loop feed return mechanism into feeding the loop out from the loop introduction needle, and has also moved the suture thread feed mechanism into feeding the thread out from the suture thread introduction needle.

Figure 6C:
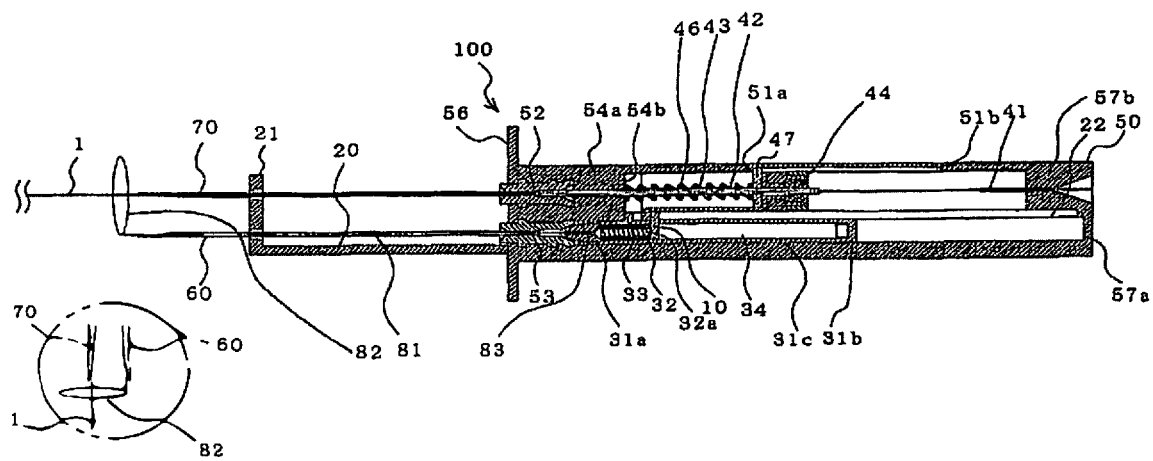

Referring now to FIG. 6C, the pushing operation 6 is illustrated in which a release of the clamping of the suture thread 1 that has been set out occurs. When the operation part 10 is moved further forwards by the practitioner, the compression of the first elastic member 32 and the forwards movement of the suture thread feed part 45 continue. However, the second hollow member 42 does not move any further forwards because the movement regulating member 47 runs into the stopper 51a. If the suture thread feed part 45 is moved further forwards in this state, the second hollow member 42 penetrates the suture thread clamping member 44. When this happens, the clamping of the suture thread 1 is released and the suture thread 1 is once again free. That is, the suture thread 1 no longer moves forwards. Meanwhile, on the loop feed/return mechanism 30 side, only the first elastic member 32 is compressed while the shape of the loop 82 is maintained. The state of the suture thread 1 having passed through the inside of the loop 82 is therefore maintained.

Figure 7A:
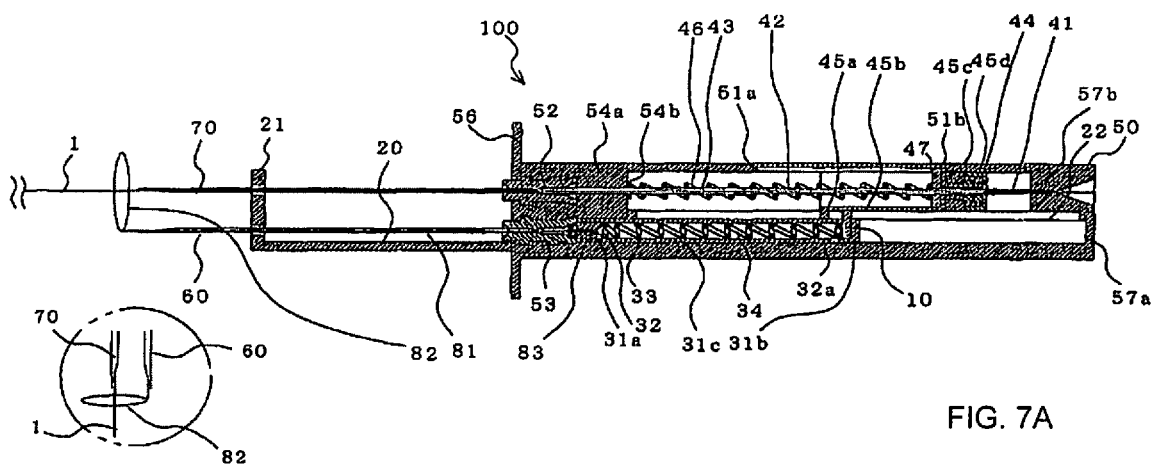
FIGS. 7A-7C illustrate a schematic view in cross section showing, in simplified form, the procedure for operating the medical suturing instrument according to one or more embodiments of the invention.

Referring now to FIG. 7A, the return operation 1 is illustrated in which a start of a backwards movement of each part occurs. When the force towards the tip end applied at the operation part 10 by the practitioner is released, the compressed state of the first elastic member 32 and the second elastic member 46 is lifted. When the compressed state of the first elastic member 32 is lifted, the operation part 10 is pushed by the first elastic member 32 and moves backwards. The operation part 10 then abuts the base end part 31b of the loop feed/return part 31. The second hollow member 42 penetrates the suture thread clamping member 44, and therefore the second hollow member 42 is also moved backwards together with the suture thread clamping member 44. After this, the backwards movement of the suture thread clamping member 44 together with the second hollow member 42, whereof the movement is regulated by the movement regulating member 47 running into the stopper 51b, is stopped for a time.

It should be noted that the figures show an exemplary case in which the suture thread feed part 45 is moved backwards by the lifting of the compressed state of the second elastic member 46, but the suture thread feed part 45 can still move backwards without the second elastic member 46, as will be described later.

Figure 7B:
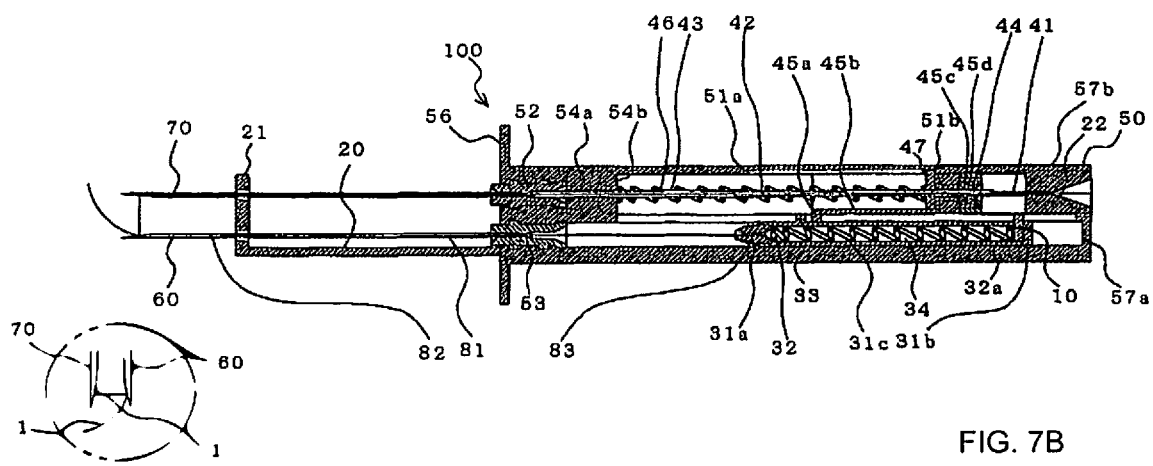

Referring now to FIG. 7B, the return operation 2 is illustrated with a start of return of loop 82 and an end of gripping of the suture thread 1. When the operation part 10 is moved further backwards by the practitioner, the operation part 10 pushes the base end part 31b of the loop feed/return part 31, and the loop feed/return part 31 starts to move backwards. As the loop feed/return part 31 moves backwards, the loop 82 starts to be accommodated inside the loop introduction needle 60, in such a way that the suture thread 1 is drawn to the tip end of the loop introduction needle 60.

In accordance with some embodiments, a position of the operation part at a completion of return operation 2 is referred to as a second position. According to these embodiments, with the operation part in the second position, loop feed/return mechanism and the suture thread feed mechanism are retracted to return the loop at least partly inside the loop introduction needle after the suture thread has been gripped by the loop. According to one embodiment, the loop is prevented from being returned fully within the loop introduction needle so long as the suture thread is gripped by the loop. In an alternate embodiment, the loop is fully retracted within the loop introduction needle while gripping the suture thread.

The suturing instrument 100 makes it possible to adjust the timing such that the base end surface of the first abutment part 33 and the tip end surface of the second abutment part 45a come into abutment after the suture thread 1 has been gripped at the tip end of the loop introduction needle 60, or at the same time as the suture thread 1 is gripped at the tip end of the loop introduction needle 60. Consequently, before the suture thread 1 is gripped at the tip end of the loop introduction needle 60, the base end surface of the first abutment part 33 and the tip end surface of the second abutment part 45a are not yet in abutment. That is to say, the backwards force of the operation part 10 is not transmitted to the suture thread feed part 45 before the suture thread 1 has been gripped at the tip end of the loop introduction needle 60.

The base end surface of the first abutment part 33 and the tip end surface of the second abutment part 45a come into abutment after the suture thread 1 has been gripped at the tip end of the loop introduction needle 60, or at the same time as the suture thread 1 is gripped at the tip end of the loop introduction needle 60 (see return operation 3 below). That is to say, in the suturing instrument 100, the feeling when the suture thread 1 is gripped at the tip end of the loop introduction needle 60 is transmitted to the practitioner by way of the operation part 10 before the feeling when the base end surface of the first abutment part 33 and the tip end surface of the second abutment part 45*a* come into abutment is transmitted to the practitioner by way of the operation part 10, or at the same time as the feeling when the base end surface of the first abutment part 33 and the tip end surface of the second abutment part 45*a* come into abutment is transmitted to the practitioner by way of the operation part 10.

According to one embodiment, the first abutment part 33 is included as a projection included in the loop feed/return mechanism 30 while the second abutment part 45*a* is included as a projection included in the suture feed thread mechanism 40. In various embodiments, either or both of the first abutment 33 and the second abutment 45*a* are configured to extend radially from the loop feed/return mechanism 30 and the suture feed thread mechanism 40, respectively. According to some embodiments, the abutments 33, 45*a* are in the form of tabs or other similar structure.

When the suture thread 1 has been gripped at the tip end of the loop introduction needle 60, the loop forming part 80 cannot enter the loop introduction needle 60, so neither the loop feed/return part 31 nor the suture thread feed part 45 can move any further backwards, even if the practitioner attempts to move the operation part 10 backwards.

In this state, when the suturing instrument 100 is removed, the suture thread 1 is smoothly guided because it is free, and the suture thread 1 reaches a state of having passed through the internal organ wall and the abdominal wall in substantially a U-shape. That is, the practitioner can make the suture thread 1 reach a state of having passed through the internal organ wall and the abdominal wall in substantially a U-shape simply by means of pushing operations (pushing operations 1-6) and return operations (return operations 1 and 2).

Figure 7C:
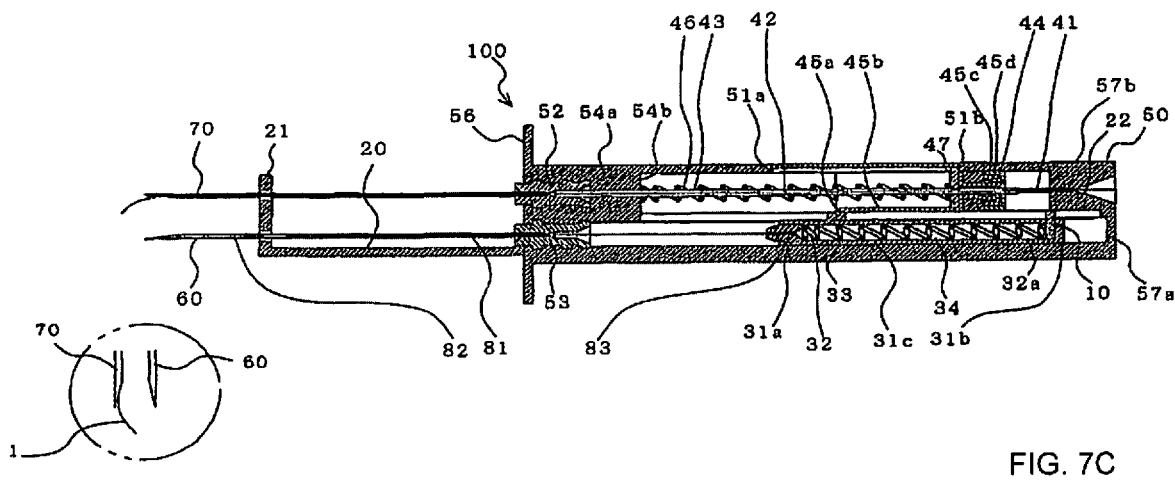

Referring now to FIG. 7C, the return operation 3 is illustrated in which an abutment of the first abutment part 33 and the second abutment part 45A occurs. The practitioner then uses the cutting tip of the suture thread introduction needle 70 which has been withdrawn to outside the body or another cutting means (scissors, cutter etc.) to cut the suture thread 1. The excess suture thread 1 gripped at the tip end of the loop introduction needle 60 is then removed. When this is done, the loop forming part 80 can enter the loop introduction needle 60 and the loop feed/return part 31 can move backwards.

In this state, when the operation part 10 is moved further backwards, the loop feed/return part 31 moves backwards and the first abutment part 33 and second abutment part 45*a* come into abutment. The backwards force of the operation part 10 is transmitted to the second abutment part 45*a* by way of the first abutment part 33, and the suture thread feed part 45 moves backwards.

Referring again to FIG. 4 a return operation 4 is illustrated in which each component returns to an initial state. When the suture thread feed part 45 moves further backwards, the suture thread clamping member 44 is withdrawn from the second hollow member 42 and then over-mounts the first hollow member 41, in the same way as in the initial state. The suture thread 1 remains free. That is, the suture thread 1 does not move.

Meanwhile, the loop feed/return part 31 moves backwards, under the force of the first elastic member 32 and the backwards force applied to the operation part 10, until the backwards movement of the suture thread feed part 45 stops. When the suture thread clamping member 44 returns to the initial state, the parts return to the initial state together (see FIG. 4).

Accordingly, the same state as the initial state is reached, in which the suture thread 1 is inserted up to the tip end of the suture thread introduction needle 70, and therefore the internal organ wall can be fixed any number of times using the above procedure. Moreover, if the suture thread 1 is projecting further towards the tip end than the cutting edge of the suture thread introduction needle 70 after the suture thread 1 has been cut, the same state as the initial state may be set by pulling the suture thread 1 towards the base end by hand.

Figure 8A:
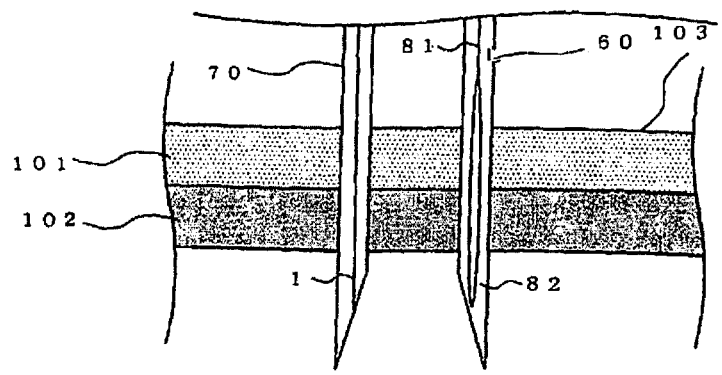
FIGS. 8A-8C illustrate the action of the medical suturing instrument according to one or more embodiments of the invention.
Figure 8B:
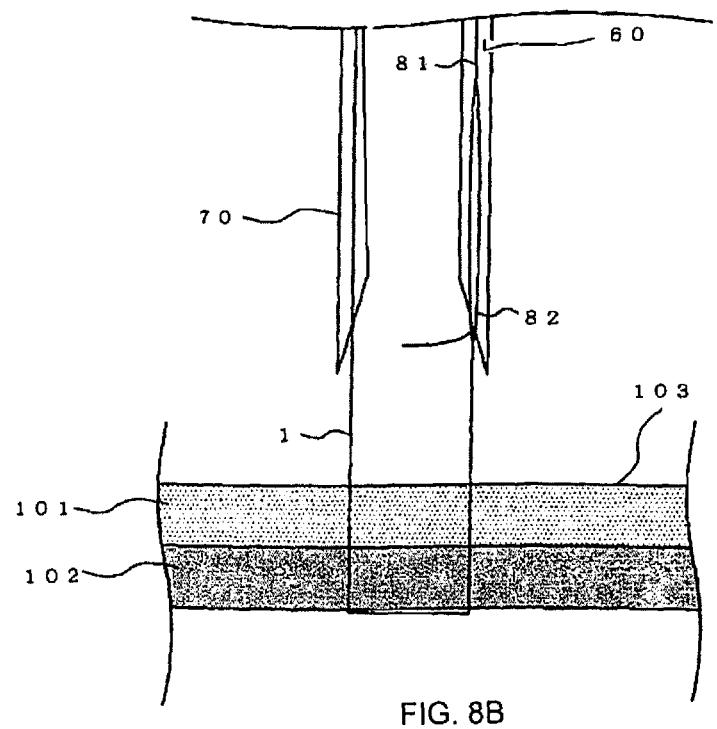
Figure 8C:
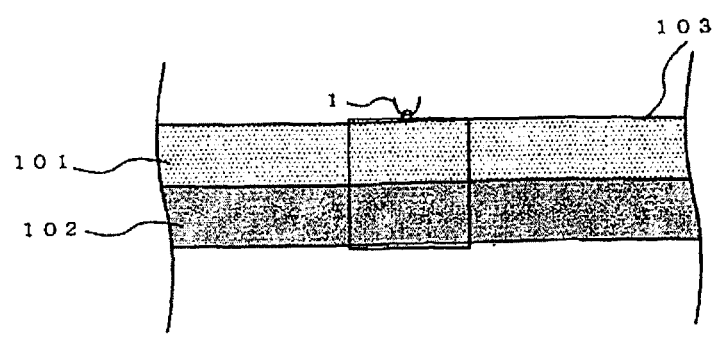

FIGS. 8A-8C provide an explanatory diagram to illustrate the action of the suturing instrument 100. The action of the suturing instrument 100 will be described in line with the flow of the procedure employing the suturing instrument 100, with reference to FIG. 8. In the description given here, a patient's abdominal wall 101 and internal organ wall 102 (e.g. stomach wall) are fixed using the suturing instrument 100.

The practitioner first of all inserts an endoscope orally or nasally into the patient's internal organ (e.g. the stomach). The practitioner then expands the internal organ by filling the internal organ with a gas (e.g. carbon dioxide). As a result, the internal organ wall 102 is placed in close contact with the abdominal wall 101. Next, the skin 103 is sterilized, including the site to be pierced by the loop introduction needle 60 and the suture thread introduction needle 70. The position of the internal organ is then confirmed by the light emitted from the endoscope, and a local anaesthetic is administered at this site.

Next, the suturing instrument 100 is prepared: the loop 82 of the loop forming part 80 is accommodated inside the loop introduction needle 60, and the suture thread 1 is accommodated inside the suture thread introduction needle 70 (the state shown in FIG. 4). At this point, the suture thread 1 is accommodated inside the suture thread introduction needle 70 in such a way as not to project from the tip end of the suture thread introduction needle 70. The loop introduction needle 60 and the suture thread introduction needle 70 of the suturing instrument 100 are then made to pierce the patient's abdominal wall 101, and the loop introduction needle 60 and the suture thread introduction needle 70 are made to project into the internal organ from the internal organ wall 102 (FIG. 8A).

Once this state has been confirmed using the endoscope, the practitioner moves the operation part 10 forwards. The practitioner then carries out the series of operations shown in FIGS. 5A to 7C, and the suture thread 1 is exposed outside the body (FIG. 8B). That is, the suture thread 1 is in the situation of passing through the internal organ wall 102 and the abdominal wall 101 in substantially a U-shape. Finally, the practitioner cuts the suture thread 1 which has been withdrawn to outside the body and ties the two ends of the suture thread 1 (FIG. 8C). The internal organ wall 102 and the abdominal wall 101 are fixed by this tying.

The suturing instrument 100 is then once again made to pierce the body substantially parallel to the position of the tie at a prescribed distance of around 20-30 mm, for example, and the internal organ wall 102 and the abdominal wall 101 are fixed. That is, the suture thread 1 functions as an organopexy tool in order to fix the internal organ wall 102 and the abdominal wall 101, so it is possible to easily form a fistula which is used when inserting a fistula catheter. In this process, by using a length of suture thread 1 which provides for multiple operations, it is possible to use the suturing instrument 100 continuously.

The suturing instrument 100 makes it possible to fix internal organs any number of times until the suture thread 1 runs out, without the need to insert the suture thread 1 into the suturing instrument 100 every time. Furthermore, the suturing instrument 100 makes it possible to pass the suture thread 1 in a U-shape through the internal organ wall 102 and the abdominal wall 101 simply by means of operations involving pushing and pulling of the operation part 10 (pushing operations (pushing operations 1-6) and return operations (return operations 1, 2)). Specifically, the practitioner can pass the suture thread 1 through the internal organ wall 102 and the abdominal wall 101 simply by carrying out an operation to move the operation part 10 forwards and an operation until a feeling of the suture thread 1 being gripped at the tip end of the loop introduction needle 60 is transmitted, so the procedure which the practitioner needs to follow can be considerably simplified. In addition, the suture thread 1 is fed out once the loop 82 has already opened into an annular shape, so the suture thread 1 can be reliably inserted into the loop 82.

Accordingly, the burden on the practitioner can be considerably reduced and the ease of use is markedly improved. Furthermore, the procedure itself can be carried out very simply, and therefore not only is the ease of use improved, but the ease of handling is also considerably improved. In addition to the procedure being simple, the suture thread 1 can also be securely gripped, and therefore it is possible to minimize the number of times piercings are made, so this can contribute not only to reducing the burden on the practitioner, but also to reducing the burden on the patient. In addition, the first elastic member 32 is provided, so the action of the first elastic member 32 enables the pushing operations to be smoothly carried out and improves stability during the procedure.

Furthermore, the force when the suture thread feed part 45 is moved backwards by way of the operation part 10 is directly transmitted to the practitioner as the feeling when the suture thread 1 is gripped at the tip end of the loop introduction needle 60. Consequently, it is a simple matter for the practitioner to judge that the suture thread 1 has been gripped at the tip end of the loop introduction needle 60, and the ease of use is further improved.

Further aspects of the present invention pertain to facilitating use of any one or more embodiments of the disclosed medical suturing instruments. For example, one or more aspects of the invention can pertain to providing a medical suturing instrument having a housing; a loop introduction needle which is provided at a tip end of the housing; a suture thread introduction needle for housing a suture thread, which is provided at the tip end of the housing a prescribed distance apart from the loop introduction needle and substantially parallel thereto; a loop forming part which has a loop formed at a tip end thereof and is movably inserted into the loop introduction needle; a loop feed/return mechanism provided inside the housing for moving the loop forming part; a suture thread feed mechanism provided inside the housing for feeding out the suture thread; and an operation part which is provided inside the housing or projecting from the housing, and which moves the loop feed/return mechanism and the suture thread feed mechanism; wherein movement of the operation part is transmitted to the loop feed/return mechanism, and the loop is fed out from a tip end of the loop introduction needle, movement of the operation part is transmitted to the suture thread feed mechanism, and the suture thread is fed out from a tip end of the suture thread introduction needle, after this, movement of the operation part in the opposite direction is transmitted to the loop feed/return mechanism, and the loop is housed inside the loop introduction needle, and the movement of the operation part in the opposite direction is transmitted to the suture thread feed mechanism after the suture thread has been gripped by the loop at the tip end of the loop introduction needle or at the same time as the suture thread is gripped by the loop at the tip end of the loop introduction needle. In other cases, the method of facilitating can involve providing a medical suturing instrument having a housing; a loop introduction needle at a tip end of the housing; a suture thread introduction needle having a portion of a suture thread disposed therein, the suture thread introduction needle disposed at the tip end of the housing at a prescribed distance apart from the loop introduction needle and oriented substantially parallel thereto; a loop forming part having a loop in a tip end thereof, the loop insertable into the loop introduction needle; a loop feed/return mechanism inside the housing and operatively disposed to move the loop forming part; a suture thread feed mechanism inside the housing and operatively disposed to feed the suture thread; and an operation part operatively coupled to the loop feed/return mechanism and the suture thread feed mechanism, wherein the operation part has a first position that moves the loop feed/return mechanism into feeding the loop out from the loop introduction needle, and moves the suture thread feed mechanism into feeding the thread out from the suture thread introduction needle, and wherein the operation part has a second position that retracts the loop feed/return mechanism and the suture thread feed mechanism to return the loop at least partly inside the loop introduction needle after the suture thread has been gripped by the loop.

It should be noted that the above described embodiments provide an exemplary case in which it is assumed that the suturing instrument 100 is used repeatedly, but the suturing instrument 100 is not necessarily used repeatedly. That is to say, it is equally possible to insert the suture thread 1 having a length corresponding to a single procedure, without using the suturing instrument 100 repeatedly.

DESCRIPTION OF REFERENCE NUMERALS

1 suture thread, 10 operation part, 20 support rod, 21 flat plate part, 22 groove, 30 loop feed/return mechanism, 31 loop feed/return part, 31a tip end part, 31b base end part, 31c side wall part, 32 first elastic member, 32a base end part, 33 first abutment part, 34 accommodation part, 40 suture thread feed mechanism, 41 first hollow member, 42 second hollow member, 43 third hollow member, 44 suture thread clamping member, 45 suture thread feed part, 45a second abutment part, 45b side wall extension part, 45c main body part, 45d fitting part, 46 second elastic member, 47 movement regulating member, 50 housing, 51a stopper, 51b stopper, 52 support part, 53 support part, 54a thick-walled part, 54b tip end inner wall surface, 55 guide hole, 56 flange part, 57a base end inner wall surface, 57b base end inner wall surface, 60 loop introduction needle, 70 suture thread introduction needle, 80 loop forming part, 81 rod-like shaft, 82 loop, 83 base end fixing part, 100 suturing instrument, 101 abdominal wall, 102 internal organ wall, 103 skin.

The invention claimed is:

1. A medical suturing instrument comprising:
a housing;
a loop introduction needle extending distally from the housing;
a suture thread introduction needle extending distally from the housing in spaced-apart relation relative to the loop introduction needle;
a first abutment part operably disposed within the housing in transverse relation to the loop introduction needle;
a second abutment part operably disposed within the housing in transverse relation to the suture thread introduction needle; and
an operation part operably coupled to the housing, the operation part selectively movable relative to the housing in an actuation direction an initial distance to move the first abutment part in the actuation direction to feed a loop out from the loop introduction needle, the operation part further movable in the actuation direction an additional distance to move the second abutment part in the actuation direction to feed a suture thread out from the suture thread introduction needle, the operation part movable in a retraction direction opposite the actuation direction to retract the loop into the loop introduction needle.

2. The medical suturing instrument according to claim 1, further comprising a loop feed/return mechanism operably disposed within the housing and including the first abutment part, the loop feed/return mechanism configured to feed the loop out from the loop introduction needle in response to the movement of the first abutment part in the actuation direction.

3. The medical suturing instrument according to claim 2, wherein the loop feed/return mechanism is retracted upon movement of the operation part in the retraction direction.

4. The medical suturing instrument according to claim 1, further comprising a suture thread feed mechanism operably disposed within the housing and including the second abutment part, the suture thread feed mechanism configured to feed the suture thread out from the suture thread introduction needle in response to movement of the first abutment part in the actuation direction.

5. The medical suturing instrument according to claim 4, wherein the suture thread feed mechanism is retracted upon movement of the operation part in the retraction direction.

6. The medical suturing instrument according to claim 4, wherein contact between the first abutment part and the second abutment part as the operation part is moved in the retraction direction transmits rearward force to the suture thread feed mechanism.

7. The medical suturing instrument according to claim 1, wherein the loop introduction needle and the suture thread introduction needle are disposed in substantially parallel orientation relative to one another.

8. The medical suturing instrument according to claim 1, wherein an elastic member is operably coupled between the operation part and the first abutment part.

9. The medical suturing instrument according to claim 8, wherein the elastic member is substantially uncompressed during movement of the operation part the initial distance such that movement of the operation part is transmitted into movement of the first abutment part in the actuation direction.

10. The medical suturing instrument according to claim 8, wherein the elastic member is increasingly compressed during movement of the operation part the additional distance such that the first abutment part remains substantially stationary during movement of the operation part the additional distance.

11. A suturing method, comprising:
inserting a loop introduction needle and a suture thread introduction needle into a body in spaced-apart relation relative to one another;
moving an operating part in an actuation direction an initial distance to move a first abutment part in the actuation direction to feed a loop out from the loop introduction needle;
moving the operation part in the actuation direction an additional distance to move a second abutment part in the actuation direction to feed a suture thread out from the suture thread introduction needle;
moving the operation part in a retraction direction opposite the actuation direction to retract the loop into the loop introduction needle after the suture thread has been gripped by the loop;
withdrawing the loop introduction needle and the suture thread introduction needle from the body.

12. The method according to claim 11, further comprising releasing the suture thread from the loop.

13. The method according to claim 11, wherein the a loop introduction needle and the suture thread introduction needle are inserted into the body in parallel orientation relative to one another.

14. The method according to claim 11, wherein an elastic member operably coupled between the operation part and the first abutment part is substantially uncompressed during movement of the operation part the initial distance.

15. The method according to claim 11, wherein an elastic member operably coupled between the operation part and the first abutment part is increasingly compressed during movement of the operation part the additional distance such that the first abutment part remains substantially stationary during movement of the operation part the additional distance.

16. The method according to claim 11, wherein moving the operating part in the actuation direction the initial distance moves the first abutment part of a loop feed/return mechanism such that the loop feed/return mechanism feeds the loop out from the loop introduction needle.

17. The method according to claim 11, wherein moving the operation part in the actuation direction the additional distance moves the second abutment part of a suture thread feed mechanism such that the suture thread feed mechanism feeds the suture thread out from the suture thread introduction needle.

18. A medical suturing instrument comprising:
a loop introduction needle;
a suture thread introduction needle extending in spaced-apart relation relative to the loop introduction needle;
a first abutment part operably disposed in transverse relation to the loop introduction needle;
a second abutment part operably disposed in transverse relation to the suture thread introduction needle;
an operation part selectively movable in an actuation direction an initial distance to move the first abutment part in the actuation direction to feed a loop out from the loop introduction needle, the operation part further movable in the actuation direction an additional distance to move the second abutment part in the actuation direction to feed a suture thread out from the suture thread introduction needle, the operation part movable in a retraction direction opposite the actuation direction to retract the loop into the loop introduction needle; and an elastic member operably coupled between the operation part and the first abutment part, wherein the elastic member is substantially uncompressed during movement of the operation part the initial distance such that movement of the operation part is transmitted into movement of the first abutment part in the actuation direction, and wherein the elastic member is compressed during movement of the operation part the additional distance such that the first abutment part remains substantially stationary during movement of the operation part the additional distance.

19. The medical suturing instrument according to claim 18, further comprising a loop feed/return mechanism including the first abutment part, the loop feed/return mechanism configured to feed the loop out from the loop introduction needle in response to the movement of the first abutment part in the actuation direction.

20. The medical suturing instrument according to claim 18, further comprising a suture thread feed mechanism including the second abutment part, the suture thread feed mechanism configured to feed the suture thread out from the suture thread introduction needle in response to movement of the first abutment part in the actuation direction.

* * * * *